United States Patent
Stein et al.

(10) Patent No.: US 10,998,107 B1
(45) Date of Patent: May 4, 2021

(54) EXTRACTANTS AND EXTRACTANT COMPOSITIONS FOR RADIOISOTOPE AND METAL RECOVERY

(71) Applicant: Los Alamos National Security, LLC, Los Alamos, NM (US)

(72) Inventors: Benjamin W. Stein, Los Alamos, NM (US); Tara E. Mastren, Salt Lake City, UT (US); Michael E. Fassbender, Los Alamos, NM (US); Stosh A. Kozimor, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 16/118,308

(22) Filed: Aug. 30, 2018

Related U.S. Application Data

(60) Provisional application No. 62/553,007, filed on Aug. 31, 2017.

(51) Int. Cl.
| | |
|---|---|
| *G21F 9/12* | (2006.01) |
| *B01D 15/20* | (2006.01) |
| *G21F 9/00* | (2006.01) |
| *C07C 327/42* | (2006.01) |
| *B01D 15/36* | (2006.01) |
| *G21G 1/00* | (2006.01) |

(52) U.S. Cl.
CPC .............. *G21F 9/12* (2013.01); *B01D 15/203* (2013.01); *B01D 15/363* (2013.01); *C07C 327/42* (2013.01); *G21F 9/007* (2013.01); *G21G 1/001* (2013.01); *G21G 2001/0094* (2013.01)

(58) Field of Classification Search
CPC .......................................................... G21F 9/12
See application file for complete search history.

(56) References Cited

U.S. PATENT DOCUMENTS

| | | |
|---|---|---|
| 7,157,022 B2 | 1/2007 | Horwitz et al. |
| 2015/0292061 A1 | 10/2015 | Fassbender et al. |

FOREIGN PATENT DOCUMENTS

| | | | |
|---|---|---|---|
| JP | 03237149 A | * | 10/1991 |

OTHER PUBLICATIONS

Huang et al., "Extraction of palladium(II) from nitric acid solutions with diglycolthioamide," *Hydrometallurgy*, 156 (2015) 6-11.

* cited by examiner

*Primary Examiner* — Melissa S Swain

(57) ABSTRACT

Disclosed herein are embodiments of an extractant that can be used for chromatographic isolation of radioisotopes and/or metal species. The extractant can be combined with a support medium to provide an extractant composition that selectively and efficiently binds particular radioisotopes and/or metal species. Also disclosed herein are embodiments of a method for using the disclosed extractant embodiments, as well as embodiments of a method for making the extractant and extractant composition.

21 Claims, 6 Drawing Sheets

EXTRACTANTS AND EXTRACTANT COMPOSITIONS FOR RADIOISOTOPE AND METAL RECOVERY

CROSS REFERENCE TO RELATED APPLICATION

This application claims priority to U.S. Provisional Application No. 62/553,007, filed Aug. 31, 2017, which is incorporated herein by reference in its entirety.

ACKNOWLEDGMENT OF GOVERNMENT SUPPORT

This invention was made with government support under Contract No. DE-AC52-06NA25396 awarded by the U.S. Department of Energy. The government has certain rights in the invention.

FIELD

Disclosed herein are embodiments of an extractant and an extractant composition comprising the extractant and a support material, as well as embodiments of methods for making and using the extractant and the extractant composition.

BACKGROUND

Current extraction methods for separation and isolation of metals and radioisotopes typically employ extraction chromatography methods utilizing thiophosphinate, thiophosphines, and/or diglycolamide (or "DGA"); however, such methods typically are non-specific for particular metals/radioisotopes and thus their efficiency for separation/isolation is greatly reduced by the presence of competing species present in samples. Conventional extraction techniques and materials in precious metal recovery exhibit even less selectivity and/or efficiency due to the very low concentrations of precious metals in samples relative to common species, such as iron or sodium. There exists a need in the art for extractant species and extractant compositions that exhibit high selectivity and efficiency in separation chemistry.

SUMMARY

Disclosed herein are embodiments of a composition comprising an extractant and a support material. The compositions can be used to isolate particular metals, radioisotopes, and metal ions. Also disclosed herein are compound embodiments that can be used as the extractants in the extractant compositions described herein. Also disclosed are method embodiments for using the extractant and extractant compositions. In some embodiments, the method comprises exposing a liquid sample to an extractant composition comprising a support material and an extractant having a structure satisfying a formula provided herein and wherein the liquid sample is exposed to the composition for a time sufficient to promote formation of a complex between the extractant composition and a radioisotope, a metal, and/or any ion thereof present in the liquid sample; separating the complex from the liquid sample; exposing the complex to a solution having a pH sufficient to promote dissociation of the radioisotope, the metal, or any ion thereof from the extractant composition; and isolating the radioisotope, the metal, or any ion thereof.

The foregoing and other objects, features, and advantages of the present disclosure will become more apparent from the following detailed description, which proceeds with reference to the accompanying figures.

DETAILED DESCRIPTION

I. Overview of Terms

Figure 1:
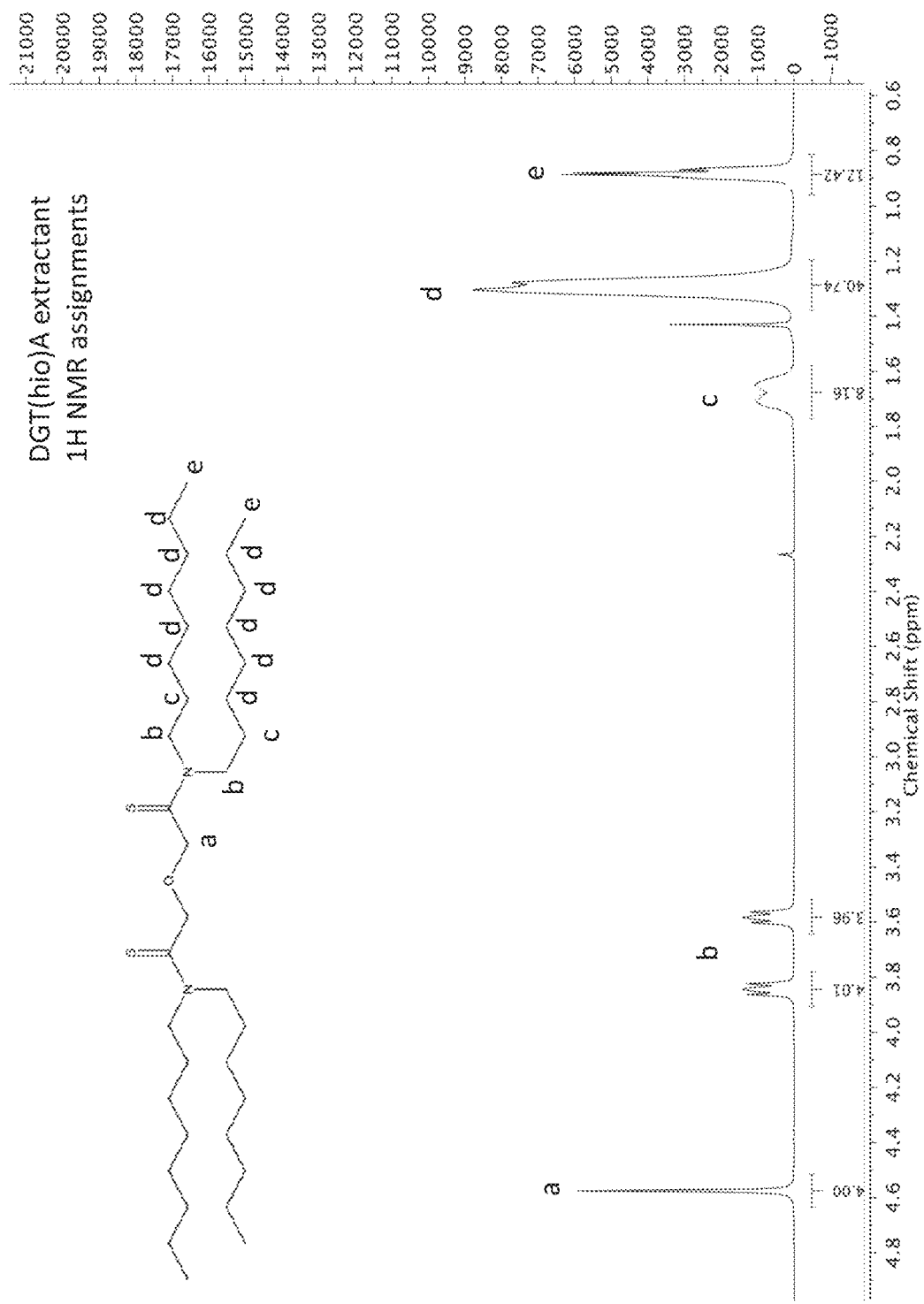
FIG. 1 is a $^1$H-NMR spectrum of an extractant embodiment described herein.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" and "provide" to describe the disclosed methods. These terms are high-level abstractions of the actual steps that are performed. The actual steps that correspond to these terms will vary depending on the particular implementation and are readily discernible by one of ordinary skill in the art.

Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms and abbreviations are provided:

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aryl: An aryl group that is or can be coupled to an extractant embodiment disclosed herein, wherein the aryl group is or becomes coupled through an aliphatic group.

Aliphatic-heteroaryl: A heteroaryl group that is or can be coupled to an extractant embodiment disclosed herein, wherein the heteroaryl group is or becomes coupled through an aliphatic group.

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (for example, cycloalkenyl), cis, or trans (for example, E or Z).

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (for example, alkane). An alkyl group can be branched, straight-chain, or cyclic (for example, cycloalkyl).

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (for example, cycloalkynyl).

Alkylaryl/Alkenylaryl/Alkynylaryl: An aryl group that is or can be coupled to an extractant embodiment disclosed herein, wherein the aryl group is or becomes coupled through an alkyl, alkenyl, or alkynyl group, respectively.

Alkylheteroaryl/Alkenylheteroaryl/Alkynylheteroaryl: A heteroaryl group that is or can be coupled to an extractant embodiment disclosed herein, wherein the heteroaryl group is or becomes coupled through an alkyl, alkenyl, or alkynyl group, respectively.

Amide: —C(O)NR'R" or —NR'C(O)— wherein each of R' and R" independently is selected from hydrogen, aliphatic, heteroaliphatic, aromatic, aliphatic-aromatic, or heteroaliphatic-aromatic, or any combination thereof.

Aromatic: A cyclic, conjugated group or moiety of, unless specified otherwise, from 5 to 15 ring atoms having a single ring (for example, phenyl, pyridinyl, or pyrazolyl) or multiple condensed rings in which at least one ring is aromatic (for example, naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

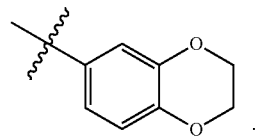 [SMILES: *c1ccc2c(c1)OCCO2]

However, in certain examples, context or express disclosure may indicate that the point of attachment is through a non-aromatic portion of the condensed ring system. For example,

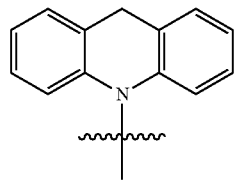

An aromatic group or moiety may comprise only carbon atoms in the ring, such as in an aryl group or moiety, or it may comprise one or more ring carbon atoms and one or more ring heteroatoms comprising a lone pair of electrons (for example, S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aryl, heteroaryl, other functional groups, or any combination thereof.

Complex: When used in the context of a "complex" formed between an extractant composition and a metal, metal ion, or radioisotope, the term "complex" means that the extractant and/or the extractant composition is ionically and/or covalently bound to the metal, metal ion, or radioisotope. In some embodiments, a complex is formed by one or more ionic interactions (for example, electrostatic interactions) between the extractant and the metal, or the metal ion, or a radioisotope (or any combination thereof). In some embodiments, a complex is formed by one or more covalent bonds between the extractant and the metal, or a metal ion, or a radioisotope (or any combination thereof).

Extractant: A chemical compound capable of forming a complex with a radioisotope and/or a metal species. Extractant embodiments described herein comprise at least one thioamide functional group and more typically comprise two thioamide groups. In an independent embodiment, an extractant is not or is other than a diglycolamide compound.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaliphatic-aryl: An aryl group that is or can be coupled to an extractant embodiment disclosed herein, wherein the aryl group is or becomes coupled through a heteroaliphatic group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl-aryl/Heteroalkenyl-aryl/Heteroalkynyl-aryl: An aryl group that is or can be coupled to an extractant embodiment disclosed herein, wherein the aryl group is or becomes coupled through a heteroalkyl, heteroalkenyl, or heteroalkynyl group, respectively.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen, such as aliphatic, heteroaliphatic, aryl, heteroaryl, other functional groups, or any combination thereof.

Radioisotope: An atom that has more nuclear energy than its parent atom. Radioisotopes can be naturally occurring, produced as a result of nuclear fission, and/or synthetic.

Support Material: A component, typically a solid component, that is combined with an extractant embodiment to form an extractant composition. Exemplary support materials can include, but are not limited to, a polymeric resin, an inorganic, particle-based material, a bead, a crystalline compound, an amorphous compound, or any combination thereof.

Thioamide: —C(S)NR$^a$R$^b$ wherein each of R$^a$ and R$^b$ independently is selected from hydrogen, aliphatic, aromatic, or aliphatic-aromatic. In an independent embodiment, at least one R$^a$ or one R$^b$ is aliphatic, heteroaliphatic, aromatic, aliphatic-aromatic, or heteroaliphatic-aromatic. Exemplary thioamides are described herein.

A person of ordinary skill in the art would recognize that the definitions provided above are not intended to include impermissible substitution patterns (for example, methyl substituted with 5 different groups, and the like). Such impermissible substitution patterns are easily recognized by a person of ordinary skill in the art. In formulas and specific compounds disclosed herein, a hydrogen atom is present and completes any formal valency requirements (but may not necessarily be illustrated) wherever a functional group or other atom is not illustrated. For example, a phenyl ring that is drawn as

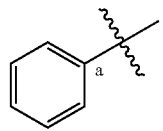 [SMILES: *c1ccccc1]

comprises a hydrogen atom attached to each carbon atom of the phenyl ring other than the "a" carbon, even though such hydrogen atoms are not illustrated.

Any functional group disclosed herein and/or defined above can be substituted or unsubstituted, unless otherwise indicated herein.

II. Introduction

Extraction methods used to separate and isolate precious metals typically include solvent extraction methods and/or chromatography methods requiring hard oxygen donor extractants (for example, diglycolamide). These extraction methods, however, suffer from poor selectivity and efficiency. The inventors of the present disclosure have discovered extractant embodiments and extractant compositions that can be used in chromatography-based extraction techniques to provide selective isolation and/or separation of precious metals and/or radioisotopes. Extractant composition embodiments described herein utilize a soft-donor-based extractant compound and a support material that have not been used in the art for chromatographic separation of selected metals from samples. Furthermore, the extractant and extractant composition embodiments described herein exhibit high selectivity and efficiency for isolating rare metals (and radioisotopes thereof) used in the medical field, such as niobium and protactinium, that are not attained using conventional extractants, such as diglycolamide-based extractants. For example, in some embodiments, the extractant and extractant compositions described herein do not exhibit affinity for the species from which niobium and protactinium are obtained, such as thorium, and also do not exhibit affinity for other metals, such as lanthanides.

III. Extractant and Extractant Composition Embodiments

Disclosed herein are embodiments of an extractant. In particular disclosed embodiments, the extractant can be used in extraction chromatography. The extractant embodiments disclosed herein comprise functional groups that facilitate the ability of the extractant to isolate particular species of interest that are not isolated by conventional extractant compounds used in the art, such as diglycolamides. In particular disclosed embodiments, the extractant comprises thioamide functional groups. In particular embodiments, the extractant has a structure satisfying Formula I below.

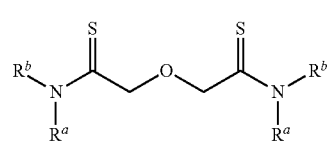

Formula I

With reference to Formula I, each R$^a$ independently can be selected from hydrogen, aliphatic, heteroaliphatic, aromatic, aliphatic-aromatic, or heteroaliphatic-aromatic, and each R$^b$ independently can be selected from hydrogen, aliphatic, heteroaliphatic, aromatic, aliphatic-aromatic, or heteroaliphatic-aromatic, provided that at least one $R^a$ or one $R^b$ is aliphatic, heteroaliphatic, aromatic, aliphatic-aromatic, or heteroaliphatic-aromatic. In some embodiments, each $R^a$ independently can be selected from aliphatic, heteroaliphatic aryl, aliphatic-aryl, or heteroaliphatic-aryl. In yet some additional embodiments, each $R^a$ independently can be alkyl, alkenyl, alkynyl, heteroalkyl, heteroalkenyl, heteroalkynyl, aryl, alkyl-aryl, alkenyl-aryl, alkynyl-aryl, heteroalkyl-aryl, heteroalkenyl-aryl, or heteroalkynyl-aryl. In particular disclosed embodiments, each $R^a$ independently can be lower alkyl, such as decyl, nonyl, octyl, septyl, hexyl, pentyl, butyl, propyl, ethyl, or methyl, wherein these groups can be straight chain, branched chain, or cyclic versions of such groups. In particular exemplary embodiments, each $R^a$ independently can be octyl or 2-ethylhexyl.

In any of the above-described embodiments, $R^b$ can be selected from any of the groups recited above for $R^a$. In particular disclosed embodiments, each $R^a$ can be the same or different from the other $R^a$. In additional embodiments, each $R^b$ can be the same or different from the other $R^b$. In yet additional embodiments, $R^a$ and $R^b$ can be the same or different from one another. In some embodiments, each $R^a$ and each $R^b$ can be the same. In some embodiments, an $R^a$ group can be bound to an $R^b$ group that is attached to the same nitrogen atom as the $R^a$ group so as to form a cyclic moiety including the nitrogen atom to which the $R^a$ and $R^b$ groups are attached. A representative formula for such embodiments is illustrated below as Formula II. In some embodiments, the cyclic moiety can be a heterocyclic ring or a heteroaryl ring.

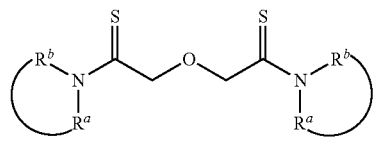

Formula II

In some embodiments, the extractant can be selected from any of the following:

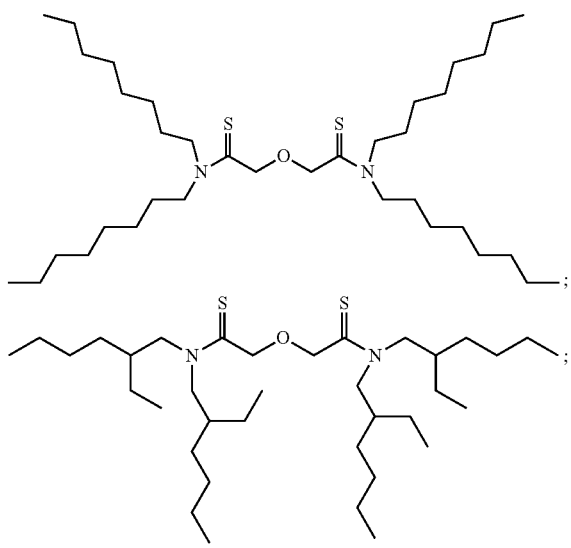

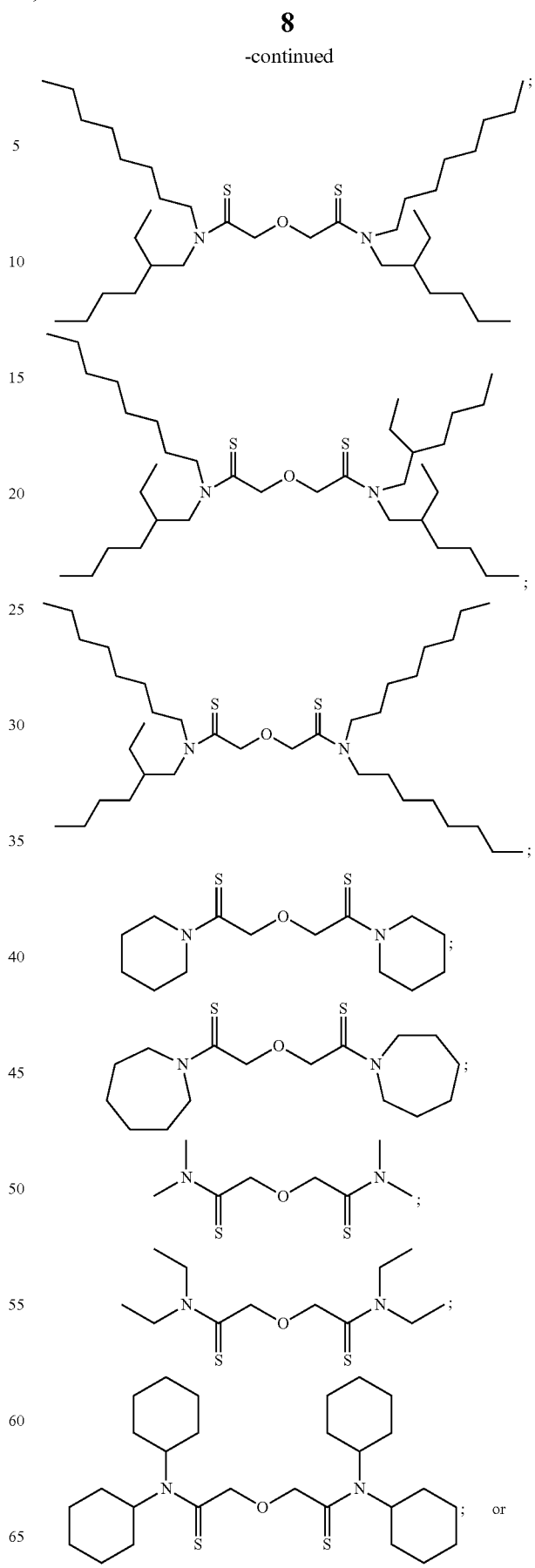

-continued

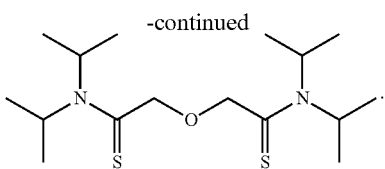

The extractant embodiments described above can be used in combination with a support material to provide an extractant composition for use in chromatography. In an independent embodiment where an extractant is used alone without a corresponding support material (such as when the extraction is conducted in liquid media only, such as with an organic liquid layer and an aqueous liquid layer), the extractant is not or is other than N,N,N',N'-tetraoctyldiglycolamide. The support material can be selected from any support material capable of being used in aqueous and/or organic solvent separations. In some embodiments, the support material can be a resin, such as an organic, polymeric resin material. In other embodiments, the support material can be an inorganic, particle-based material. Exemplary polymeric resin materials include, but are not limited to, acrylic resins (for example, a CG-71 resin, which is an insoluble aliphatic (acrylic ester) polymer; or a CG-161, CG-300, or CG-100 resin, which are styrene/divinyl benzene-containing resins), polyaromatic resins (for example, polyaromatic resins sold under the tradename AMBERLITE®), or reverse-phase (C18-functionalized) silica. Organic polymeric resins are typically used in embodiments employing water (or aqueous-based solvents) as an elution solvent. In embodiments using an aqueous elution solvent and an organic, polymeric resin, the extractant need not be covalently or ionically bound to the support material and can instead be in physical contact with the support material. In some embodiments, the support material can be an inorganic, particle-based support medium, such as silica-, silicate- (for example, Florasil®), or alumina-based particles. In some embodiments, the particle-based support material can be a silica gel. Exemplary silica gels include, but are not limited to, spherical, irregular, or mesoporous silica gels (for example, Millipore-Sigma Silica Gel 60 or SBA-15 type mesoporous silica). These inorganic supports can be of a variety of particle and pore sizes, depending upon the application. Such support materials are useful for embodiments where an organic solvent is used as an elution solvent. In such embodiments, the extractant can be chemically bound to the silica gel support so as to prevent stripping of the extractant upon exposure of the support and extractant to an organic solvent. Silica gels can be covalently functionalized by reaction with alkoxysilyl containing reagents, which creates a covalent silicon-oxygen bond between the support material and the functionalizing molecule.

IV. Methods

Disclosed herein are methods of using the extractant embodiments described herein. In particular disclosed embodiments, the extractant embodiments can be used alone or in combination with a support material as chromatographic agents for separating particular species of interest (for example, radioisotopes, metal isotopes, precious metals, and any combination thereof) from other species present in a sample. In some embodiments, the extractant embodiments described herein are combined with a support material, such as the support materials described above, and then placed in a column. In yet additional embodiments, the extractant and the support material can be combined in any suitable reaction housing, such as a beaker, a flask, or other suitable container that provides a sufficient volume for the components to mix. The column can be any column typically used in the field of metal extraction/separation. Column dimensions can be selected based on the amount of material to be passed through the column and/or the amount of the species of interest that can be complexed with the extractant. In some embodiments, small column volumes (for example, 1 mL to 10 mL) can be used due to the particularly high selectivity of the disclosed extractant and extractant composition embodiments for species that are present in small amounts in a sample. Solutions may be flowed through the column utilizing gravity or pressure, depending upon the application. The resin is not limited to a column of a particular size, and can be used on columns in the range of mL to L. Herein, a column includes any container which allows for simultaneous retention of the resin and a free flow of solution. In other embodiments the resin material can simply be contacted with a solution of metal ions and removed by any convenient method, for example, filtration or centrifugation. Methods describing how to make the extractant and extractant compositions are provided herein.

After preparing a column comprising the extractant or the extractant composition embodiments or after adding these components to a suitable container, a sample is introduced into the column or container, typically using a solvent, such as an aqueous solvent or an organic solvent. In some embodiments, however, the sample can be added neat. The sample can comprise one or more species of interest, such as the metal species described below (or any ion and/or radioisotope thereof). In some embodiments, the extractant/extractant composition is exposed to the sample for a sufficient period of time to form a complex between a metal (and/or an ion or radioisotope thereof) and the extractant composition, particularly between the metal (and/or an ion or radioisotope thereof) and the extractant. In some embodiments, the metal (and/or the ion or radioisotope thereof) can be a metal of interest that is to be isolated and retained after the method is performed, or the metal (and/or the ion or radioisotope thereof) can be a species that is not desired and that is solely isolated so as to separate it from a species of interest. In particular embodiments, the time sufficient to promote formation of the complex is the amount of time needed for the liquid sample to pass through a chromatographic column comprising the composition by way of gravitational flow. This time period can range depending on the size/volume of the column used.

After a period of time, the complex formed between the extractant/extractant composition and the metal (and/or the ion or radioisotope thereof) is separated from the liquid sample using an elution step. Elution can comprise allowing the liquid sample to flow from the column and/or actively flowing the liquid sample from the column (for example, by applying pressure to the column). In embodiments where the species of interest form a complex with the extractant/extractant composition, the species of interest can first be separated from the liquid sample and then a further elution step can be used to separate the species of interest from the extractant/extractant composition. In some embodiments, an acidic aqueous solution can be used for the further elution step. The acidic aqueous solution may comprise a mineral acid, such as hydrochloric acid, hydrofluoric acid, hydrobromic acid, hydriodic acid, sulfuric acid, nitric acid, phosphoric acid, or a combination thereof. In some embodiments, hydrochloric acid is used. In some embodiments, a suitable concentration of the acid is used to ensure that a species binds to the extractant and/or extractant composition. The concentration may be from greater than 0.0001 M to 12 M or more, such as from 0.1 M to 12M, or from 1M to 12M, or from 3 M to 12 M, or from 4 M to 12 M, or from 6 M to 10 M. In some other embodiments, an organic solvent solution can be used for the further elution step.

The extractant and extractant composition embodiments described herein can be used for selective isolation/separation of particular species, such as metals, ions, and/or radioisotopes. For example, the disclosed extractant and extractant composition embodiments are able to selectively isolate metals (and/or ions or radioisotopes thereof) belonging to Group 3 (for example, actinium and other Group 3 metals), Group 5 (for example, niobium and other Group 5 metals), Group 10 (for example, palladium, platinum, etc.), and Group 11 (for example, silver, gold, etc.) of the periodic table, as well as other metals (for example, protactinium and uranium) and including any and all ions and radioisotopes of such metals. In some embodiments, the extractant and extractant composition embodiments can be used to provide selective isolation of the rare metals niobium and protactinium. Surprisingly, the inventors have discovered that the disclosed extractant and extractant composition embodiments described herein are able to selectively isolate each of these three rare metals preferentially over metals that often are abundant in samples typically containing niobium and/or protactinium, such as lanthanides and thorium. In some embodiments, the disclosed extractant and extractant composition embodiments exhibit high specificity for protactinium over thorium. In additional embodiments, the disclosed extractant and extractant composition embodiments exhibit high specificity for niobium, protactinium, platinum (and other Group 10 metals), and silver over other metals, such as iron or sodium, which are often found abundantly in samples. Given this selectivity, the disclosed extractant and extractant composition embodiments can be used to isolate large quantities of niobium and protactinium with minimal cost and effort.

In some embodiments, species analyzed using the method embodiments and extractant compositions described herein can exhibit different log $K_d$ values at different acid concentrations. In some embodiments, silver (or a radioisotope of silver, such as Ag-111 from irradiated thorium targets) and gold can exhibit quantitative binding (for example, log $K_d$ values of greater than 3, such as 4) under low or high concentrations of acid (for example, concentrations ranging from 0-10 M HCl). As such, silver and gold can quantitatively be recovered from the extractant compositions described herein. In some embodiments, niobium (or a radioisotope of niobium, such as $^{95}$Nb) exhibits strong binding with log $K_d$ values of greater than 2 when using acid (for example, HCl) concentrations greater than 8M. By reducing the HCl concentration to less than 6M, the niobium can easily be eluted from the extractant composition. Similarly, protactinium (or a radioisotope of protactinium, such as $^{230}$Pa) exhibits strong binding with log $K_d$ values of greater than 2 when using acid (for example, HCl) concentrations greater than 7M. By reducing the HCl concentration to less than 5M, the protactinium can easily be eluted from the extractant composition. In some embodiments, uranium (or a radioisotope of uranium, such as $^{230}$U) does not exhibit detectable binding at acid concentrations less than 8M, but can exhibit some binding (for example, log $K_d$ values of 1 or less) at acid concentrations of ≥10M. In some embodiments, palladium and platinum can exhibit strong binding (for example, log $K_d$ values greater than 2, such as 2.5 to 3) under low acid concentrations (for example, less than 1 M, such as 0.1 M) and in some embodiments, palladium can exhibit such log $K_d$ values at even higher acid concentrations (for example, up to 10M). In some embodiments, iron, nickel, and cobalt exhibit very weak binding (for example, log $K_d$ values of less than 1) when acid concentrations are low (for example, less than 4M), and exhibit stronger binding (for example, log $K_d$ values of 2-3) under high acid concentrations (for example, 6-10M). In some embodiments, antimony can exhibit weak binding (for example, log $K_d$ values of less than 1) at acid concentrations of less than 6M, and exhibit stronger binding (for example, log $K_d$ values of 1.75) under higher acid concentrations (for example, ≥8M). Lanthanides, thorium, and actinium do not exhibit any detectable binding under any conditions.

In some embodiments, the extractant and extractant composition embodiments disclosed herein can be used as $^{230}$U and/or $^{226}$Th generators. $^{226}$Th is an isotope of interest for targeted alpha therapy treatment of metastatic cancers. $^{226}$Th is generated from $^{230}$U, which is in turn generated by the decay of $^{230}$Pa. Protactinium is produced in good yield by the proton irradiation of natural thorium targets. Because the extractant and extractant composition embodiments described herein can selectively separate protactinium from thorium, they are effective in separating gram quantities of thorium from pico- to nanogram quantities of protactinium, which enables the use of very small columns for rapid throughput.

In some embodiments, the extractant and extractant composition embodiments can be used to separate fission products. Fission produces large quantities of lanthanides, which in some embodiments are not retained on columns using the extractant and extractant composition embodiments disclosed herein. As such, the disclosed chromatography methods can be used to quickly recover and quantitate soft transition metals from fission by-products. Also, because complexes with uranium are only retained under specific conditions using the disclosed extractant and extractant composition embodiments, analysis of uranium targets can be conducted. In some embodiments, the extractant and extractant composition embodiments can selectively isolate $^{95}$Nb from proton irradiated thorium targets. $^{95}$Nb is a useful radiochemical tracer and thus can be useful in the development of medical imaging techniques which utilize other radioisotopes of niobium, such as PET imaging with $^{90}$Nb; however, isolating this isotope from thorium has proven challenging using conventional chromatography resins. The disclosed extractant and extractant composition embodiments provide a cost effective alternative for selective isolation of $^{95}$Nb from thorium targets-containing samples as thorium is not retained by the extractant embodiments described herein.

In additional embodiments, the extractant and extractant composition embodiments can be used to recover precious metal catalysts from reaction mixtures. Precious metals (for example, platinum and palladium) are used in a variety of chemical disciplines as catalysts for a variety of reactions. The disclosed extractant and extractant composition embodiments can be used in a recovery method capable of isolating these precious metals from other chemical reagents. In some embodiments using very dilute HCl, platinum is strongly retained on the extractant composition embodiments comprising an extractant as described herein. Once a sample has been run through a column, the platinum can be recovered from the support in a concentrated form by using a higher concentration of HCl.

In additional embodiments, the extractant and extractant composition embodiments described herein can be used to recover precious metals from mine leachates, industrial wastes, and the like. As illustrated herein, the extractant embodiments described herein exhibit high affinity for gold and silver under all conditions. As such, these elements can be specifically stripped from mining wastes with minimal pre-treatment. Furthermore, as common metals, such as Fe and Zn, are not retained by the extractant and/or extractant composition embodiments described herein, small columns can be utilized in the extraction methods.

Also disclosed herein are embodiments of a method for making an extractant according to the present disclosure. In some embodiments, the method comprises steps illustrated below in Scheme 1. As illustrated in Scheme 1, the method can comprise reacting a 2,2'-oxydiacetyl halide starting material 100 with an amine compound 102 using a base (for example, an amine base, such as triethyl amine, diisopropylethylamine, pyridine, and the like). With reference to amine compound 102, each of $R^a$ and $R^b$ can be as described above for Formula I and each X independently can be halogen (for example, Br, Cl, F, or I). This reaction forms diamide compound 104, which can then be reacted with a reagent capable of converting the diamide compound 104 into dithioamide compound 106. In particular disclosed embodiments, the reagent can be a thionating agent, such as 2,4-bis(4-methoxyphenyl)-1,3,2,4-dithiadiphosphetane 2,4-disulfide (also known as Lawesson's reagent), thiophosphoryl chloride, elemental sulfur, phosphorodithioate, phosphorous pentasulfide ($P_2S_5$ or $P_4S_{10}$), or the like. While the method illustrated below in Scheme 1 utilizes an oxydiacetyl starting material, other methods can be used to form the dithioamide compound 106, such as reacting a dinitrile compound with a) thioacetic acid with a hydride (for example, CaH) or b) phosphorous pentasulfide; reacting a dialdehyde compound with a) an amine and elemental sulfur under microwave flash heating, or b) an n-substituted formamide and sodium sulfide; reacting a diacid with an amine and elemental sulfur, and other methods that would recognized by a person of ordinary skill in the art with the benefit of the present disclosure.

Representative embodiments of a method for making extractant embodiments are illustrated below in Schemes 2, 2A, and 2B. Another embodiment of a method for making extractant embodiments is illustrated in Schemes 3, 3A, and 3B.

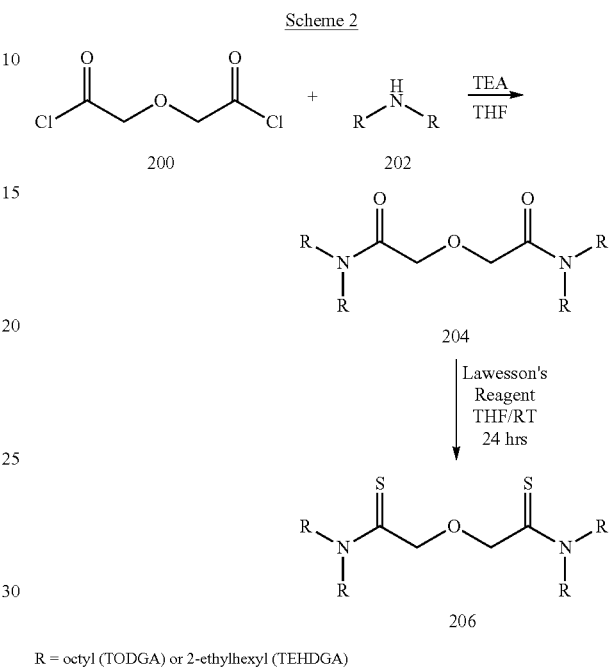

R = octyl (TODGA) or 2-ethylhexyl (TEHDGA)

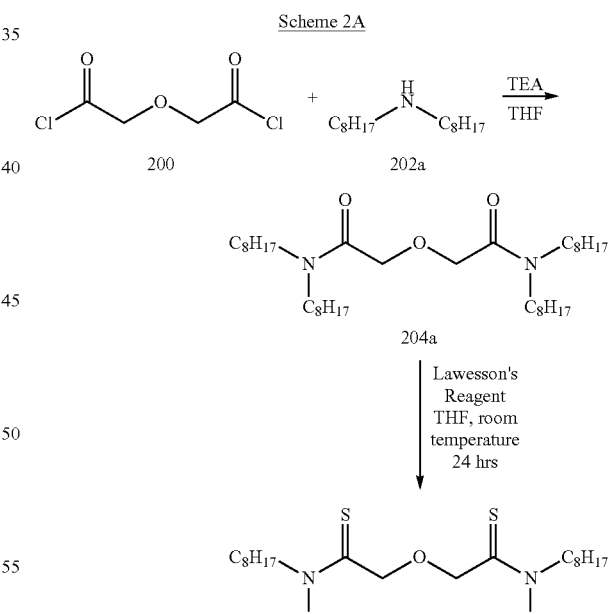

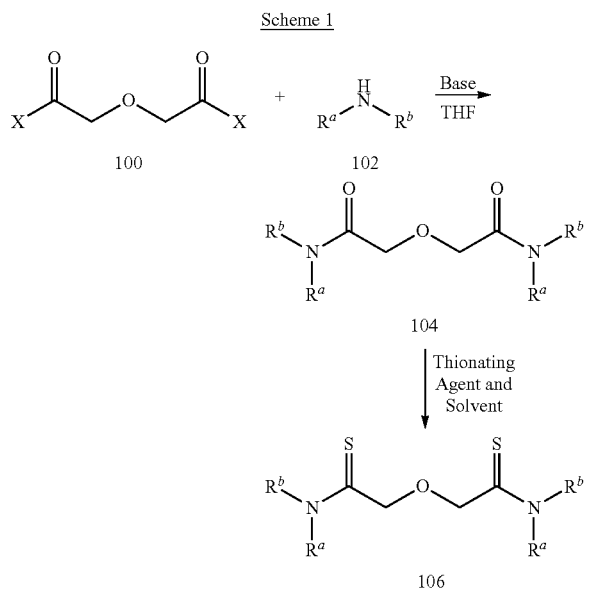

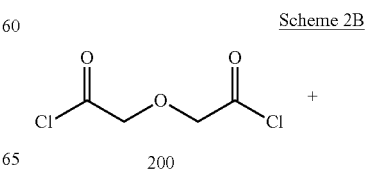

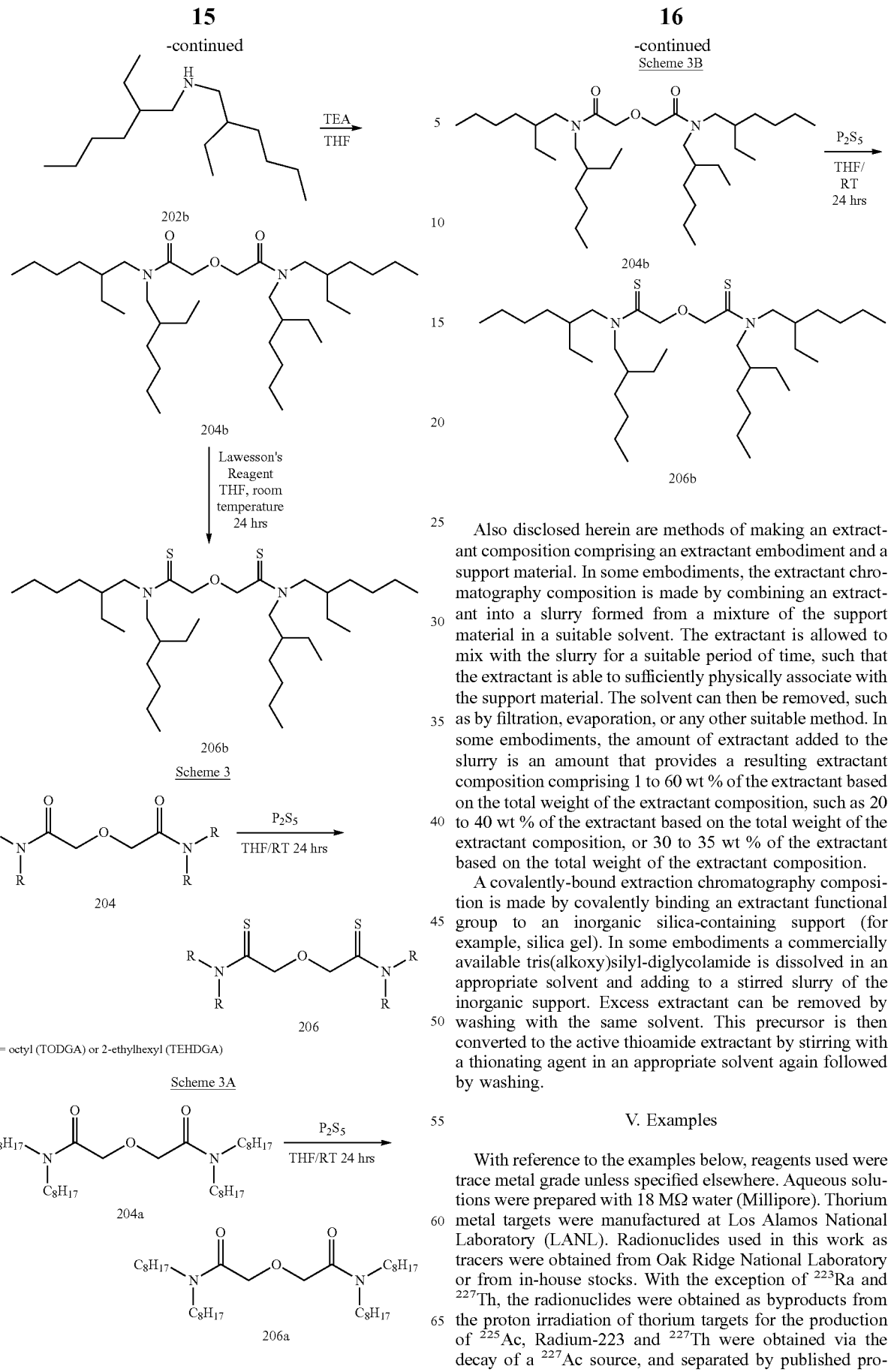

Also disclosed herein are methods of making an extractant composition comprising an extractant embodiment and a support material. In some embodiments, the extractant chromatography composition is made by combining an extractant into a slurry formed from a mixture of the support material in a suitable solvent. The extractant is allowed to mix with the slurry for a suitable period of time, such that the extractant is able to sufficiently physically associate with the support material. The solvent can then be removed, such as by filtration, evaporation, or any other suitable method. In some embodiments, the amount of extractant added to the slurry is an amount that provides a resulting extractant composition comprising 1 to 60 wt % of the extractant based on the total weight of the extractant composition, such as 20 to 40 wt % of the extractant based on the total weight of the extractant composition, or 30 to 35 wt % of the extractant based on the total weight of the extractant composition.

A covalently-bound extraction chromatography composition is made by covalently binding an extractant functional group to an inorganic silica-containing support (for example, silica gel). In some embodiments a commercially available tris(alkoxy)silyl-diglycolamide is dissolved in an appropriate solvent and adding to a stirred slurry of the inorganic support. Excess extractant can be removed by washing with the same solvent. This precursor is then converted to the active thioamide extractant by stirring with a thionating agent in an appropriate solvent again followed by washing.

V. Examples

With reference to the examples below, reagents used were trace metal grade unless specified elsewhere. Aqueous solutions were prepared with 18 MΩ water (Millipore). Thorium metal targets were manufactured at Los Alamos National Laboratory (LANL). Radionuclides used in this work as tracers were obtained from Oak Ridge National Laboratory or from in-house stocks. With the exception of $^{223}$Ra and $^{227}$Th, the radionuclides were obtained as byproducts from the proton irradiation of thorium targets for the production of $^{225}$Ac, Radium-223 and $^{227}$Th were obtained via the decay of a $^{227}$Ac source, and separated by published procedures. N,N,N',N'-Tetraoctyldiglycolamide extractant (Eichrom), Lawesson's reagent (Sigma-Aldrich), dry tetrahydrofuran (THF, Sigma-Aldrich), hexanes (Sigma-Aldrich), and silica gel (Sigma-Aldrich) were purchased. CG-71 resin was purchased from Dow chemical as a slurry in ethanol/water and converted to a dry form via filtration before use. DGA (50-100 μg) resin was obtained from Eichrom. Chloride (CL) resin (50-100 μg) was obtained from Triskem International.

Yields and purities from separation experiments were determined via γ-ray spectroscopy using an EG&G Ortec Model GMX-35200-S HPGe detector system in combination with a Canberra Model 35-Plus multichannel analyzer. Detector diameter was 50.0 mm, detector length was 53.5 mm, Be window thickness was 0.5 mm, and outer dead-layer thickness was 0.3 μm. Detector response function determination and evaluation were performed using standards of radionuclide mixtures containing $^{241}$Am, $^{109}$Cd, $^{57}$Co, $^{139}$Ce, $^{203}$Hg, $^{113}$Sn, $^{137}$Cs, $^{88}$Y, and $^{60}$Co, traceable to the National Institute of Standards and Technology (NIST) and supplied by Eckert and Ziegler. The detector was a p-type Al-windowed HPGe detector with a measured fwhm at 1333 keV of approximately 2.2 keV and a relative efficiency of about 10%. Relative total source activity uncertainties ranged from 2.6% to 3.3%. Counting dead times were kept below 10%.

Example 1

Figure 2:
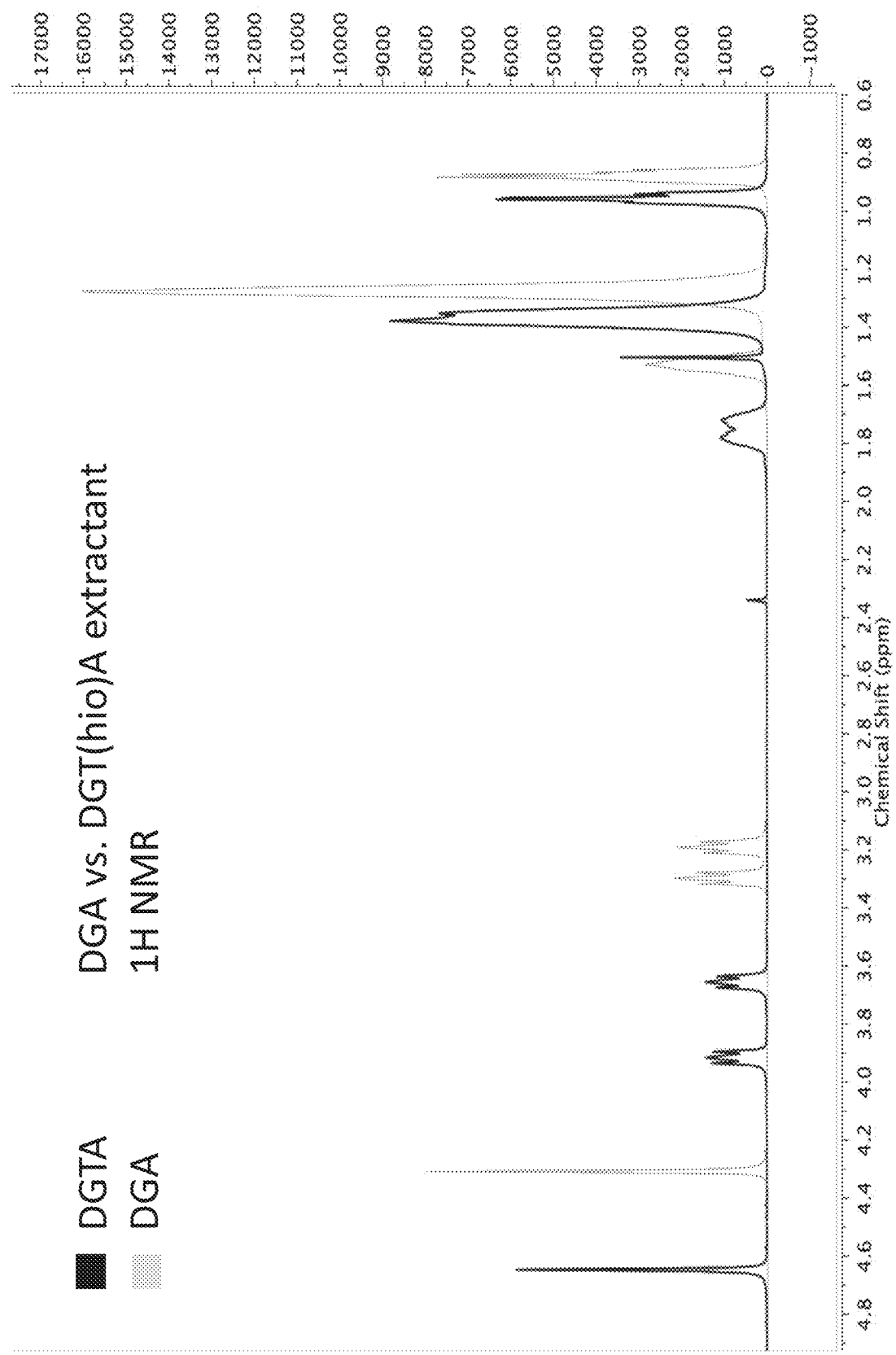
FIG. 2 is a combined $^1$H-NMR spectrum showing the spectra of a) an extractant embodiment described herein; and b) diglycolamide.
Figure 3:
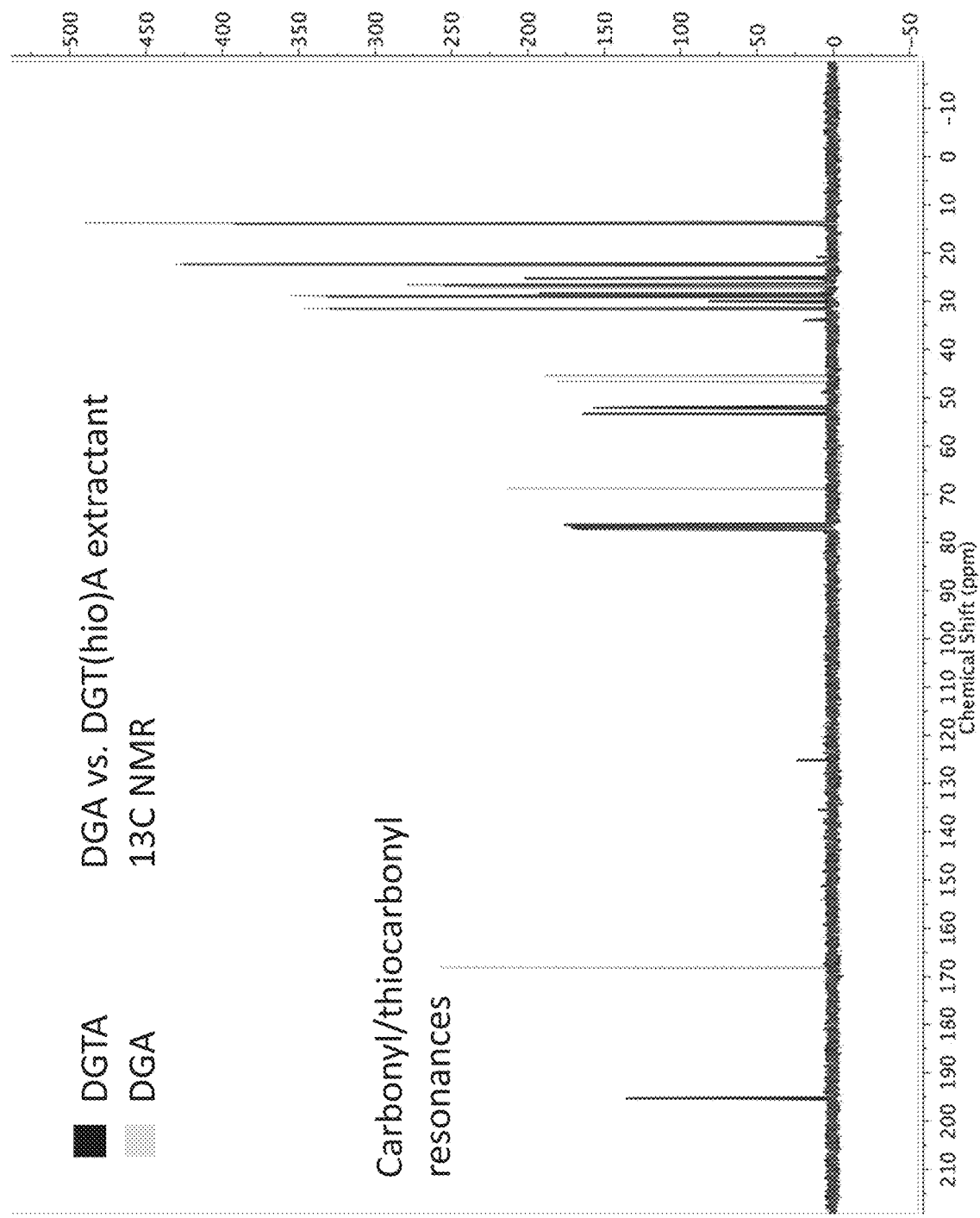
FIG. 3 is a combined $^{13}$C-NMR spectrum showing the spectra of a) an extractant embodiment described herein; and b) diglycolamide.

Synthesis of N,N,N',N'-tetraoctyldiglycolthioamide (TODGTA)—To a stirred solution of N,N,N',N'-tetraoctyldiglycolamide (1.5 g, 2.6 mmol) in 150 mL of dry THF was added 2.1 g of Lawesson's reagent. The resultant slurry was stirred at room temperature overnight with a drying tube. The yellow cloudy solution was then filtered and the solvent removed with rotary evaporation to give a gummy beige solid. The solid was then extracted with hexanes (3×10 mL) and the combined extracts were filtered through a short silica gel column (5 cm). The column was washed with 2×10 mL fractions of hexanes and the solvent was removed by rotary evaporation to give N,N,N',N'-tetraoctyldiglycolthioamide as a yellow oil (790 mg, 50% yield). $^{1}$H NMR (400 MHz, CDCl$_3$) δ 4.57 (s, 4H), 3.90-3.78 (m, 4H), 3.64-3.53 (m, 4H), 1.77-1.58 (m, 8H), 1.39-1.20 (m, 40H), 0.95-0.83 (m, 12H). The proton NMR spectrum of this compound is shown in FIG. 1. FIGS. 2 and 3 provide comparison spectra (proton, FIG. 2; and carbon, FIG. 3) of this compound and diglycolamide.

Example 2

Synthesis of N,N,N',N'-tetraoctyldiglycolthioamide (TODGTA) via phosphorous pentasulfide (P$_4$S$_{10}$) mediated thionation—To a stirred solution of N,N,N',N'-tetraoctyldiglycolamide (1.5 g, 2.6 mmol) in 150 mL of dichloromethane was added phosphorous pentasulfide (1.4 g, 2.6 mmol) and hexamethyldisiloxane (1 mL). The stirred mixture was brought to reflux for 1 hour. The solution was then cooled, filtered, the solvent was removed to give a sticky yellow solid. The solid was extracted with hexane (3×10 mL), and the combined extracts were washed with 2×50 mL portions of saturated sodium bicarbonate, separated, and passed through a 10 cm plug of silica gel, eluting with 3×10 mL portions of hexane.

Example 3

Preparation of TODGTA resin—790 mg of TODGTA was added to a slurry of 1.8 g of CG-71 resin in ethanol. The mixture was stirred on the rotary evaporator for 5 minutes before the solvent was slowly removed under vacuum. The resulting resin was 30% w/w TODGTA.

Example 4

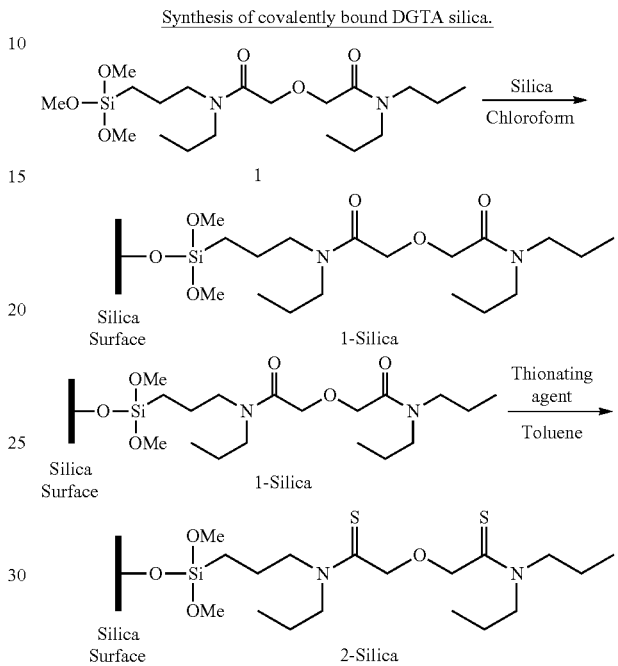

Synthesis of covalently bound DGTA silica.

The synthesis of 2-silica begins with commercially available tris-methoxysilyl DGA 1. This material is grafted onto an appropriate silica support by simple stirring at room temperature in an appropriate solvent, such as chloroform. The DGA functionalized silica is then thionated with an appropriate thionating agent, such as those described herein to give 2-silica. The material is washed with excess organic solvent and water to remove any unbound 2 and excess thionating reagent.

Example 5

Affinities for various elements were determined by dissolving the metal of interest in an appropriate concentration of hydrochloric acid and contacting with the TODGTA resin. The resin was filtered off and the metal remaining in solution was quantified via inductively coupled plasma-atomic emission spectroscopy (ICP-AES, for stable Co, Pd, Pt, Ni, Fe, Sb, Zr, and Zn.) or by gamma spectroscopy (Ag via Ag-111, Nb via Nb-91, U via U-230, and Pa via Pa-230).

As can be seen by the data provided by Table 1, extractant embodiments described herein show high specificity for certain species over others. Table 1 provides the average amount of each species present in each sample analyzed using the method described above (mg/L); different control samples were used as well as samples having different HCl concentrations). Table 1 provide the log $K_d$ values obtained from exposing samples comprising the particular indicated species to an extractant embodiment described herein. In this example, the TODGTA extractant was used for each sample. The log $K_d$ measures how much of the species is complexed with the extractant composition and how much is present in the liquid sample and can be determined by the following formula:

$$K_d = C_{solid}/C_{solution}$$

wherein $C_{solid}$ is the concentration of elements attached to the resin, in micrograms per gram of dry TODGA resin and $C_{solution}$ is the concentration of ions, in micrograms per mL of solution, which remains in solution after equilibration is established between the acid and the resin.

Higher log $K_d$ values (for example, log $K_d$ values of 2 or higher) indicate that more of the species is complexed with the extractant composition than is present in the liquid sample, whereas a lower log $K_d$ value (for example, log $K_d$ values of less than 1) indicates that less of the species is complexed with the extractant composition as compared to the liquid sample. Solely by way of example, in comparing the log $K_d$ results for iron (Fe) and platinum (Pt), it has been shown that at low acid concentrations (for example, HCl concentrations of less than 1 M, such as 0.1 M HCl), the iron does not complex with the extractant as well as the platinum. In particular, iron exhibits a log $K_d$ value less than 1 (for example, -0.35) at 0.1 M HCl, whereas the platinum exhibits a log $K_d \approx 2$ (for example, 2.09) at 0.1 M HCl.

Figure 4:
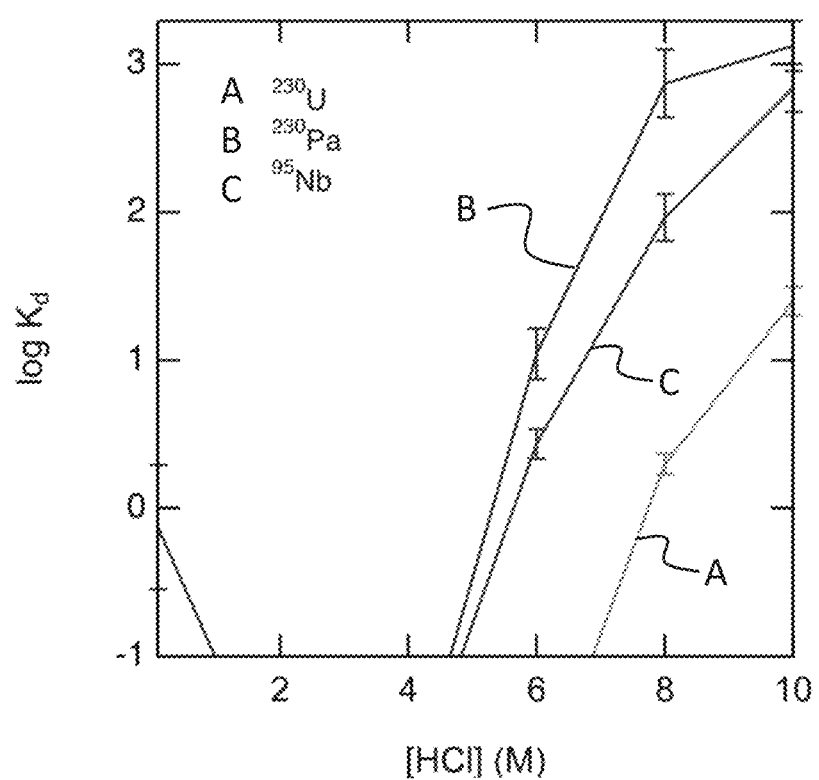
FIG. 4 is a graph of log $K_d$ as a function of HCl concentration (M) illustrating the log $K_d$ values obtained from using an extractant embodiment described herein to isolate particular radioisotopes formed by proton irradiation of a $^{232}$Thorium target.

In additional embodiments, bulk thorium can be easily separated from samples as all the thorium can be kept in the liquid sample because it does not bind to the extractant as it does not exhibit a detectable log $K_d$, whereas niobium and protactinium, for example, will exhibit strong binding (for example, log $K_d$ values greater than 2) with the extractant at high HCl concentrations (such as HCl concentrations of 6M or higher). Lanthanides and actinium also do not complex with the extractant and as such are easily separated from species of interest. Additional results showing the selectivity and log $K_d$ values for other particular species of interest, such as uranium, protactinium, and niobium, are illustrated graphically in FIG. 4.

polytetrafluoroethylene (PTFE) syringe filters (0.2 μm, EMD Millipore), and the characteristic γ-ray lines (Table 2) of $^{233}$Pa, $^{230}$U, $^{227}$Th, $^{95}$Nb, $^{223}$Ra, or $^{225}$Ac in the filtrate were measured with a high purity germanium (HPGe) detector. Determination of $^{230}$U and $^{225}$Ac was performed by waiting 5-8 hours to allow secular equilibrium to form between $^{230}$U/$^{226}$Th or $^{225}$Ac/$^{213}$Bi, respectively, and measuring characteristic $^{226}$Th or $^{213}$Bi γ-ray lines due to $^{230}$U and $^{225}$Ac having very weak γ-ray lines. The main γ-ray line for 226Th coincides with an X-ray of $^{233}$Pa; therefore, equilibrium distribution coefficients for $^{230}$U were performed separately. The total activity in the aqueous phase was calculated from the filtered solution; the activity adsorbed on the resin was determined by subtraction of total aqueous activity from the total original activity added. Distribution coefficients were calculated using the equation below $$K_d = (C_{eq1})/(C_{eq2}) = [(A_i - A_{eq})/A_{eq}] \cdot (V/m)$$

With reference to this equation, $A_i$ is the initial activity, $A_{eq}$ is the equilibrium activity in the aqueous phase, V is the volume of the equilibrium liquid phase (mL), and m is the mass of the resin (g). Considering the detection limit as dictated by signal-to-noise ratio, detector efficiency and reasonable counting time, the maximum distribution coefficient that could be measured under the experimental circumstances described above was ~105 mL·g-1 for Pa (V) and Nb (V) and ~104 mL·g-1 for all other isotopes measured.

TABLE 2

| Radionuclide | Half-life (d) | Identifying γ-ray emissions (keV) [% Intensity] |
| --- | --- | --- |
| $^{233}$Pa | 26.97 | 312 [38.6]/300 [6.62] |
| $^{230}$U ($^{226}$Th) | 20.8 | 111 [3.29] |

TABLE 1

| | Element | | | | | | | | | |
| --- | --- | --- | --- | --- | --- | --- | --- | --- | --- | --- |
| [HCl] (M) | Ag | Co | Pd | Pt | Ni | Fe | Sb | Nb[b] | U[b] | Pa[b] |
| 0.1 M | >3.0[a] | 0.15 | 2.50 | 2.09 | 0.18 | -0.35 | 0.88 | <-2[a] | <-2[a] | -0.12 |
| 2 M | >3.0[a] | 0.34 | 2.56 | 0.14 | 0.45 | -0.09 | 0.96 | <-2[a] | <2[a] | <2[a] |
| 4 M | >3.0[a] | 0.30 | 2.69 | 0.38 | 0.32 | 0.67 | 0.90 | <-2[a] | <2[a] | <2[a] |
| 6 M | >3.0[a] | 0.46 | 3.02 | 0.43 | 0.53 | 1.97 | 1.11 | 0.40 | <-2[a] | 1.04 |
| 8 M | >3.0[a] | 2.04 | 2.81 | 0.24 | 2.33 | 2.45 | 1.76 | 2.00 | 0.30 | 2.90 |
| 10 M | >3.0[a] | 2.28 | 2.75 | -0.07 | 3.24 | 2.54 | 1.75 | 2.80 | 1.40 | 3.12 |

[a] <-2 or >3 implies detection limits were exceeded.
[b] $K_d$ values determined radiochemically.

Example 6

In this example, equilibrium distribution coefficients were determined for protactinium(V), uranium(VI), thorium(IV), niobium(V), radium(II), and actinium(III) using the batch mode. Each condition was run in triplicate. Approximately 50 mg chloride resin (CL resin) or TODGTA resin (or DGTA resin) were added to pre-weighed and tared 2 mL centrifuge tubes. A total of 1 mL of liquid phase (HCl variable concentrations ranging from 0.1 to 10 M) along with a 5 μL aliquot containing 5-15 kBq of $^{233}$Pa, $^{230}$U, $^{227}$Th, $^{95}$Nb, $^{223}$Ra, and $^{225}$Ac in 0.1 M HCl were added to each tube and weighed. The mixtures were vortexed and allowed to equilibrate for 24 hours on a rocker at ambient temperature. The mixtures were filtered with 4 mm nonsterile hydrophilic TABLE 2-continued

| Radionuclide | Half-life (d) | Identifying γ-ray emissions (keV) [% Intensity] |
| --- | --- | --- |
| $^{227}$Th | 18.68 | 235 [12.3] |
| $^{95}$Nb | 34.99 | 765 [100] |
| $^{223}$Ra | 11.44 | 269 [13.7]/154 [5.62] |
| $^{225}$Ac ($^{213}$Bi) | 10.0 | 440 [26.1] |

Figure 5A:
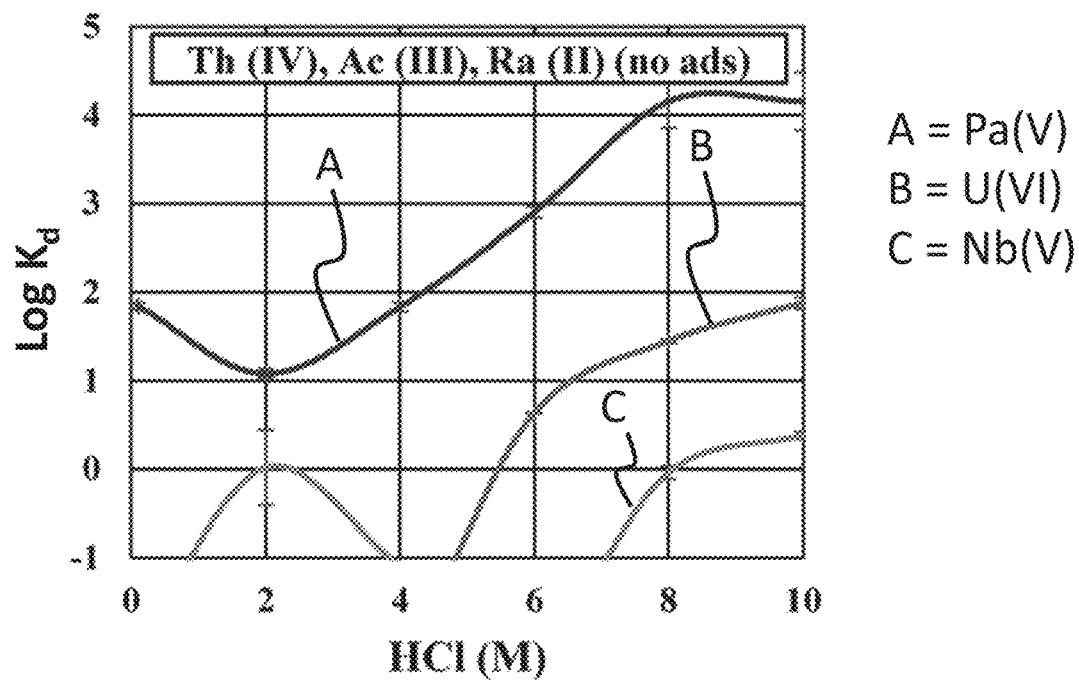
FIGS. 5A and 5B are graphs of log $K_d$ as a function of HCl concentration (M), which illustrate the equilibrium distribution coefficients $K_d$/[mL·g$^{-1}$] for protactinium, uranium, thorium, actinium, radium, and niobium on a chloride resin (FIG. 5A) and a resin comprising an extractant embodiment of the present disclosure (FIG. 5B); Th(IV), Ac(III), and Ra (II) did not adsorb onto the resins.
Figure 5B:
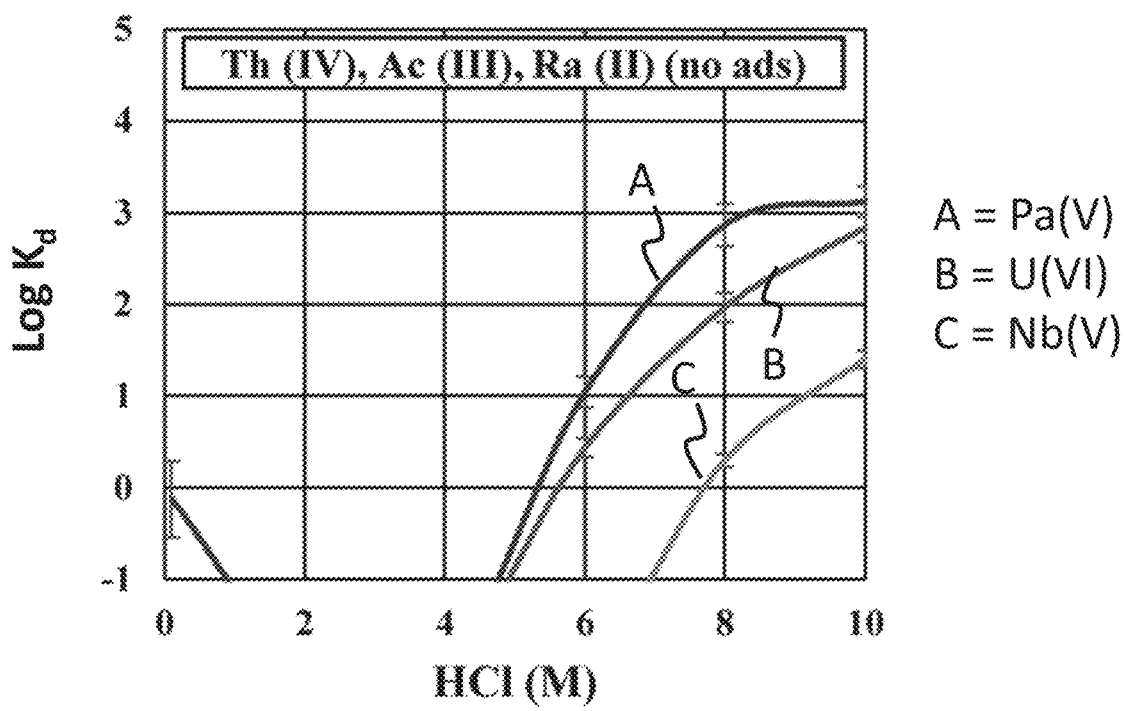

The equilibrium distribution coefficients for protactinium, uranium, thorium, niobium, radium and actinium in hydrochloric acid on CL and TODGTA resin were measured and are shown in FIGS. 5A and 5B. At high (≥8 M) hydrochloric acid concentrations, protactinium is strongly adsorbed onto both CL and TODGTA resin with $K_d$ values of 104 mL·g$^{-1}$ and 103 mL·g$^{-1}$ respectively. At low hydrochloric acid concentrations (≤4 M), $K_d$ values for protactinium are significantly lower with TODGTA having lower affinity (<0.1 mL·g$^{-1}$) than CL resin (<100 mL·g$^{-1}$). Niobium has less affinity for both resins; however, the $K_d$ values are still significant at hydrochloric acid concentrations ≥8M, limiting the ability to separate niobium from protactinium using these resins. Interestingly, TODGTA resin shows higher affinity for niobium, with $K_d$ values approaching 103 mL·g$^{-1}$, under these conditions than with CL resin. Additionally, uranium (most likely present in the form of uranyl $UO_2^{2+}$) has a $K_d$ value >10 mL·g$^{-1}$ in 10 M HCl on TODGTA resin and on CL resin its $K_d$ values remain less than 2 mL·g$^{-1}$. Thorium, radium, and actinium exhibited no affinity for either resin in any of the conditions tested. These results establish the feasibility of these resins to separate $^{230}$Pa from 230U and bulk thorium.

Example 7

Figure 6:
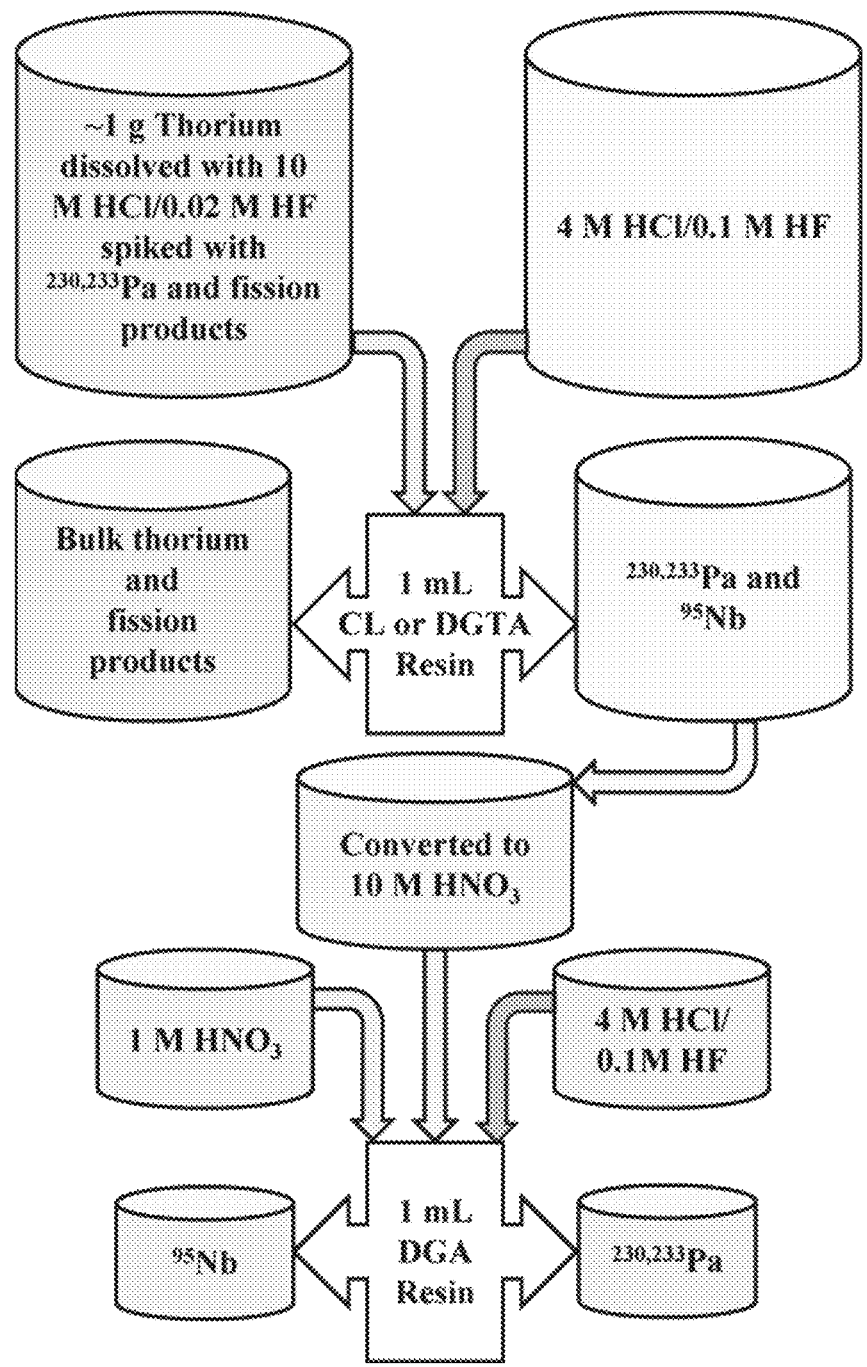
FIG. 6 is a schematic illustration of a representative separation method using an extractant embodiment of the present disclosure to separate $^{230/233}$Protactinium from bulk thorium and fission products.

As proton-induced fission coincides with the formation of $^{230}$Pa through the $^{232}$Th(p,3n) $^{230}$Pa reaction, separation studies included fission products previously identified in high energy irradiations of thorium targets. For $^{230}$Pa separation embodiments, approximately 1 g of thorium metal (>99% purity as determined via X-ray fluorescence spectroscopy) was dissolved in 40 mL of 10 M HCl/0.01 M HF. This solution was then spiked with a small aliquot of fission products as well as ~185 kBq $^{230}$Pa and contacted with a column containing 1 mL CL or TODGTA resin equilibrated with 10 M HCl. The eluent was collected (fraction 1). An additional 20 mL of 10 M HCl in 5 mL fractions (fractions 2-5) was added to the column and each fraction was collected. Protactinium-230 was then eluted with 10 mL of 4 M HCl/0.1 M HF in two 5 mL fractions (fractions 6 and 7). Fractions 6 and 7 contained the radionuclide contaminant $^{95}$Nb. Niobium-95 separation from these fractions was obtained by converting them to 10 mL of 10 M HNO$_3$ and adding to a column containing 1 mL of DGA resin equilibrated with 10 M HNO$_3$. The eluent was collected (fraction 8), and 20 mL of 1 M HNO$_3$ in 5 mL fractions (fractions 9-12) was added to the column to remove $^{95}$Nb. Protactinium-230 was then eluted with two 5 mL fractions (fractions 13-14) of 4 M HCl/0.1 M HF. Each fraction was analyzed via HPGe for radiochemical analysis. A schematic of the separation is shown in FIG. 6.

Protactinium-230/233 was separated from bulk thorium and fission products with average final recovery yields of 93±4% and 88±4% with CL resin and TODGTA resin, respectively. Protactinium radionuclidic purity reached >99.5% using both methods. The only measurable radioactive impurity consisted of $^{95}$Nb, contributing <0.5% of the total radioactivity. Due to its chemical similarity to protactinium(V), niobium(V) was difficult to separate and therefore a residual contaminant. Niobium(V), breakthrough from a $^{230}$Pa/$^{230}$U radionuclide generator could be easily removed employing normal DGA extraction chromatographic resin. All fission products, with the exception of $^{95}$Nb, were quantitatively removed using either CL or TODGTA column. Residual $^{95}$Nb was finally removed by the use of a column containing DGA resin. The TODGTA resin was capable of separating protactinium from thorium. The advantage of the use of sulfur containing resins over other reported methods is the ability to separate protactinium from both uranium and thorium in addition to a wide variety of fission products in one step with one concentration of acid. Anion exchange chromatography in combination with extraction chromatography has been used to separate protactinium from these contaminants, however the method is more complex and requires varying acid concentrations and multiple columns to obtain a comparable purity. The advantage over liquid-liquid extraction methods is the elimination of mixed waste (organic with radioactive), which can be costly to dispose of. Newer methods, such as the use of TK400 resin, have not demonstrated the ability to separate protactinium from a wide variety of fission products. The use of the disclosed sulfur-containing extractant compositions has been shown to be valuable for the selective separation of protactinium from a wide variety of contaminants and particularly for separating protactinium(V) from uranium(VI) or thorium-(IV).

VI. Overview of Several Embodiments

Disclosed herein are embodiments of a composition comprising a support material; and an extractant having a structure satisfying Formula I

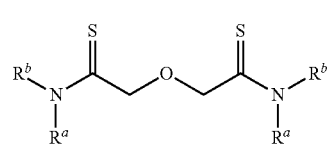

Formula I wherein each $R^a$ independently is hydrogen, aliphatic, heteroaliphatic, aromatic, aliphatic-aromatic, or heteroaliphatic-aromatic; and each $R^b$ independently is hydrogen, aliphatic, heteroaliphatic, aromatic, aliphatic-aromatic, or heteroaliphatic-aromatic, provided that at least one $R^a$ or one $R^b$ is aliphatic, heteroaliphatic, aromatic, aliphatic-aromatic, or heteroaliphatic-aromatic. In some embodiments, each $R^a$ independently is aliphatic, heteroaliphatic, aryl, aliphatic-aryl, or heteroaliphatic-aryl.

In any or all of the above embodiments, each $R^b$ independently is aliphatic, heteroaliphatic, aryl, aliphatic-aryl, or heteroaliphatic-aryl.

In any or all of the above embodiments, each $R^a$ independently is alkyl, alkenyl, alkynyl, heteroalkyl, heteroalkenyl, heteroalkynyl, aryl, alkyl-aryl, alkenyl-aryl, alkynyl-aryl, heteroalkyl-aryl, heteroalkenyl-aryl, or heteroalkynyl-aryl.

In any or all of the above embodiments, each $R^b$ independently is alkyl, alkenyl, alkynyl, heteroalkyl, heteroalkenyl, heteroalkynyl, aryl, alkyl-aryl, alkenyl-aryl, alkynyl-aryl, heteroalkyl-aryl, heteroalkenyl-aryl, or heteroalkynyl-aryl.

In any or all of the above embodiments, each $R^a$ independently is decyl, nonyl, octyl, septyl, or hexyl.

In any or all of the above embodiments, each $R^b$ independently is decyl, nonyl, octyl, septyl, or hexyl.

In any or all of the above embodiments, each $R^a$ and $R^b$ independently are octyl, 2-ethylhexyl, cyclohexyl, methyl, ethyl, or isopropyl.

In any or all of the above embodiments, each $R^a$ is the same and each $R^b$ is the same.

In any or all of the above embodiments, each $R^a$ is the same as each $R^b$.

In any or all of the above embodiments, the support material is an organic resin or an inorganic, particle-based medium.

In any or all of the above embodiments, the support material is an organic acrylic-based resin.

In any or all of the above embodiments, the support material is a silica-based support. In some embodiments, the extractant is covalently bound to the silica-based support.

In some embodiments, the extractant is

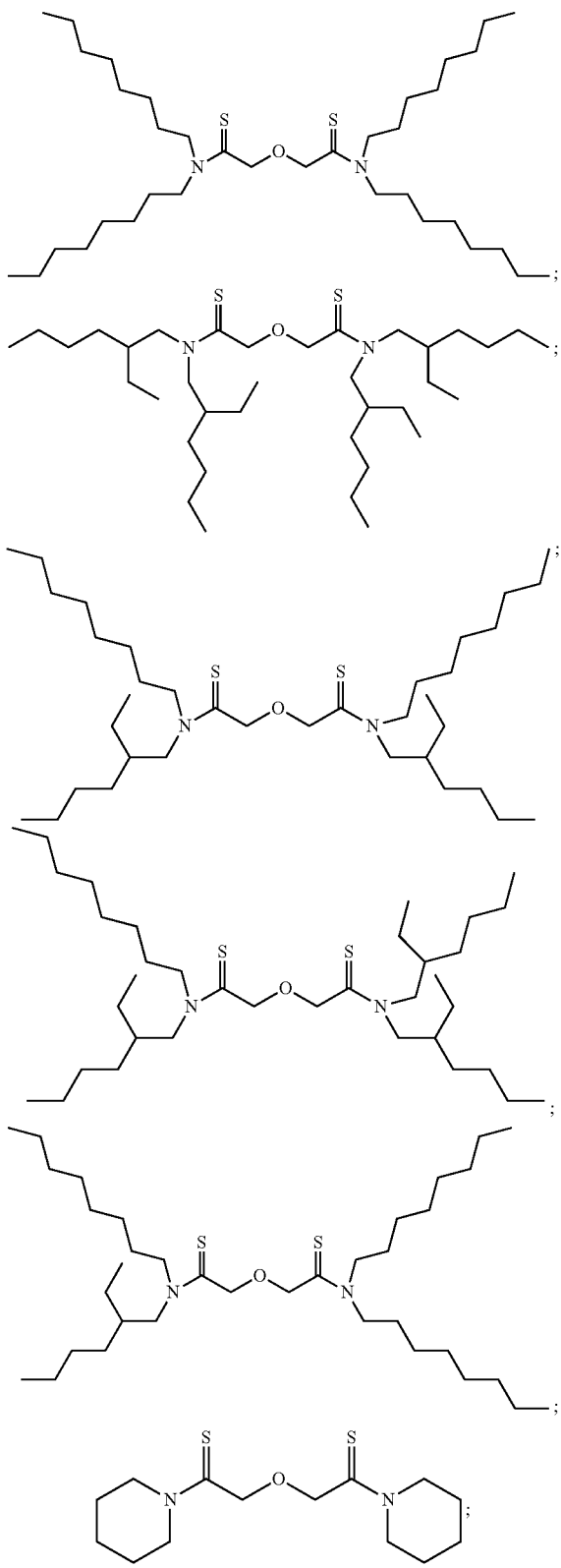

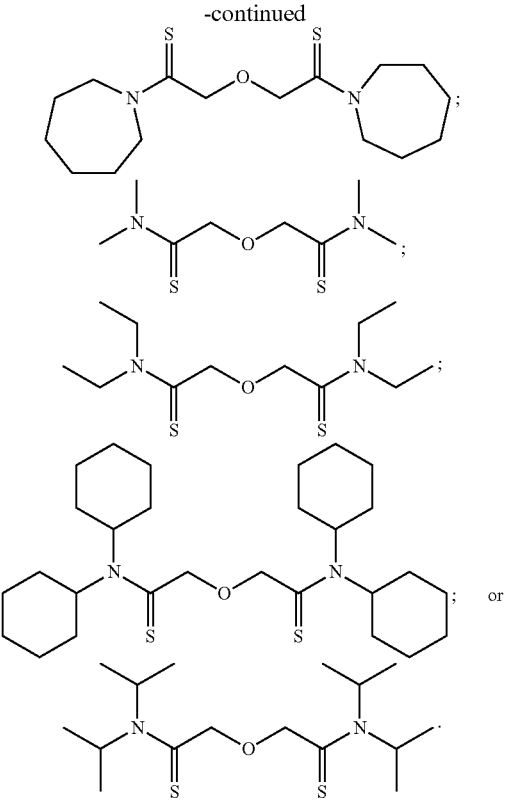

Also disclosed herein are embodiments of a method, comprising:

exposing a liquid sample to an extractant composition comprising a support material and an extractant having a structure satisfying Formula I

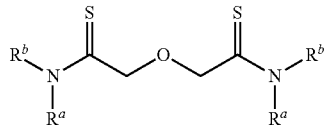

Formula I wherein each $R^a$ independently is hydrogen, aliphatic, heteroaliphatic, aromatic, aliphatic-aromatic, or heteroaliphatic-aromatic; and each $R^b$ independently is hydrogen, aliphatic, heteroaliphatic, aromatic, aliphatic-aromatic, or heteroaliphatic-aromatic, provided that at least one $R^a$ or one $R^b$ is aliphatic, heteroaliphatic, aromatic, aliphatic-aromatic, or heteroaliphatic-aromatic; and wherein the liquid sample is exposed to the composition for a time sufficient to promote formation of a complex between the extractant composition and a radioisotope, a metal, and/or any ion thereof present in the liquid sample;

separating the complex from the liquid sample; and exposing the complex to a solution having a pH sufficient to promote dissociation of the radioisotope, the metal, or any ion thereof from the extractant composition; and isolating the radioisotope, the metal, or any ion thereof.

In some embodiments, the radioisotope is protactinium, niobium, a protactinium ion, a niobium ion, or any combination thereof.

In any or all of the above embodiments, the metal is gold, platinum, silver, palladium, any ion thereof, or any combination thereof.

In any or all of the above embodiments, the sample comprises thorium, iron, zinc, any ion thereof, or any combination thereof.

Also disclosed herein are embodiments of a compound having a structure satisfying Formula I

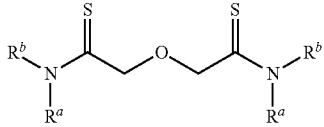

Formula I wherein each $R^a$ independently is hydrogen, aliphatic, heteroaliphatic, aromatic, aliphatic-aromatic, or heteroaliphatic-aromatic; and each $R^b$ independently is hydrogen, aliphatic, heteroaliphatic, aromatic, aliphatic-aromatic, or heteroaliphatic-aromatic, provided that at least one $R^a$ or one $R^b$ is aliphatic, heteroaliphatic, aromatic, aliphatic-aromatic, or heteroaliphatic-aromatic and further provided that the compound is not or is other than

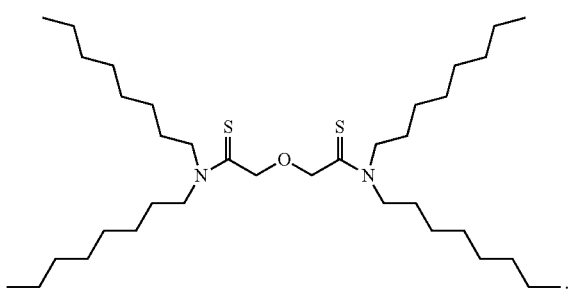 [SMILES: CCCCCCCCN(CCCCCCCC)C(=S)COCC(=S)N(CCCCCCCC)CCCCCCCC]

In some embodiments, the compound is

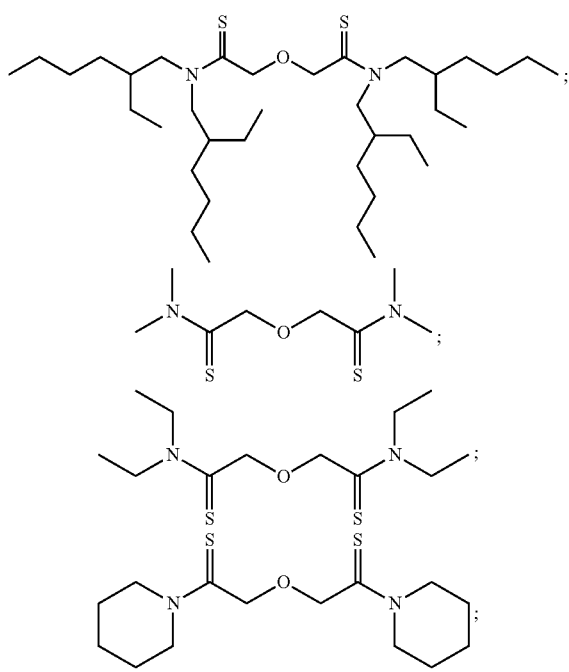

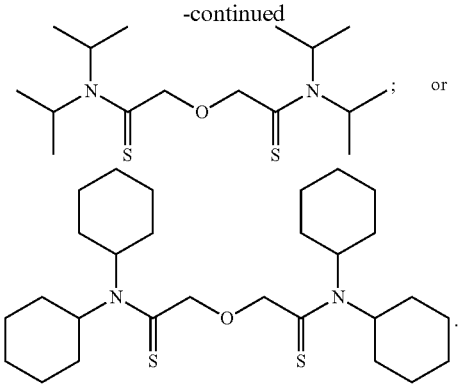

-continued

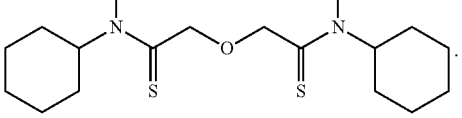

In view of the many possible embodiments to which the principles of the disclosed technology may be applied, it should be recognized that the illustrated embodiments are only preferred examples and should not be taken as limiting the scope of the present disclosure. Rather, the scope is defined by the following claims. We therefore claim as our invention all that comes within the scope and spirit of these claims.

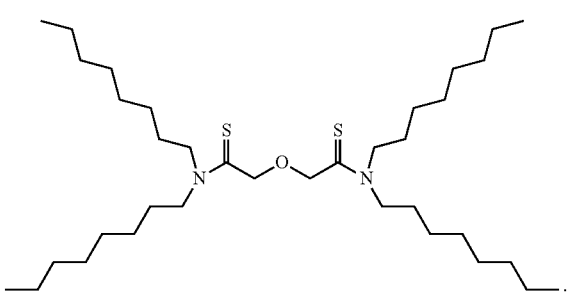 [SMILES: CCCCCCCCN(CCCCCCCC)C(=S)COCC(=S)N(CCCCCCCC)CCCCCCCC]

We claim:
1. A composition, comprising:
a support material; and
an extractant having a structure satisfying Formula I

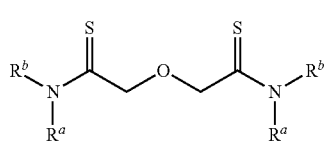

Formula I wherein each $R^a$ independently is hydrogen, aliphatic, heteroaliphatic, aromatic, aliphatic-aromatic, or heteroaliphatic-aromatic; and each $R^b$ independently is hydrogen, aliphatic, heteroaliphatic, aromatic, aliphatic-aromatic, or heteroaliphatic-aromatic, provided that at least one $R^a$ or one $R^b$ is aliphatic, heteroaliphatic, aromatic, aliphatic-aromatic, or heteroaliphatic-aromatic.

2. The composition of claim 1, wherein each $R^a$ independently is aliphatic, heteroaliphatic, aryl, aliphatic-aryl, or heteroaliphatic-aryl.

3. The composition of claim 1, wherein each $R^b$ independently is aliphatic, heteroaliphatic, aryl, aliphatic-aryl, or heteroaliphatic-aryl.

4. The composition of claim 1, wherein each $R^a$ independently is alkyl, alkenyl, alkynyl, heteroalkyl, heteroalkenyl, heteroalkynyl, aryl, alkyl-aryl, alkenyl-aryl, alkynyl-aryl, heteroalkyl-aryl, heteroalkenyl-aryl, or heteroalkynyl-aryl.

5. The composition of claim 1, wherein each $R^b$ independently is alkyl, alkenyl, alkynyl, heteroalkyl, heteroalkenyl, heteroalkynyl, aryl, alkyl-aryl, alkenyl-aryl, alkynyl-aryl, heteroalkyl-aryl, heteroalkenyl-aryl, or heteroalkynyl-aryl.

6. The composition of claim 1, wherein each $R^a$ independently is decyl, nonyl, octyl, septyl, or hexyl.

7. The composition of claim 1, wherein each $R^b$ independently is decyl, nonyl, octyl, septyl, or hexyl.

8. The composition of claim 1, wherein each $R^a$ and $R^b$ independently are octyl, 2-ethylhexyl, cyclohexyl, methyl, ethyl, or isopropyl.

9. The composition of claim 1, wherein each $R^a$ is the same and each $R^b$ is the same.

10. The composition of claim 1, wherein each $R^a$ is the same as each $R^b$.

11. The composition of claim 1, wherein the support material is an organic resin or an inorganic, particle-based medium.

12. The composition of claim 1, wherein the support material is an organic acrylic-based resin.

13. The composition of claim 1, wherein the support material is a silica-based support.

14. The composition of claim 13, wherein the extractant is covalently bound to the silica-based support.

15. The composition of claim 1, wherein the extractant is

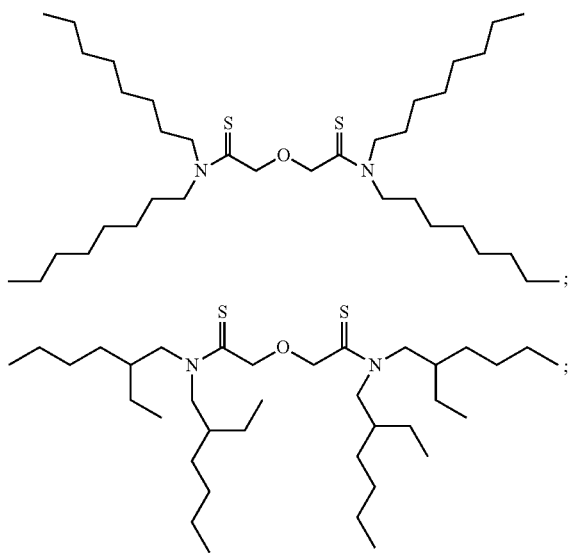

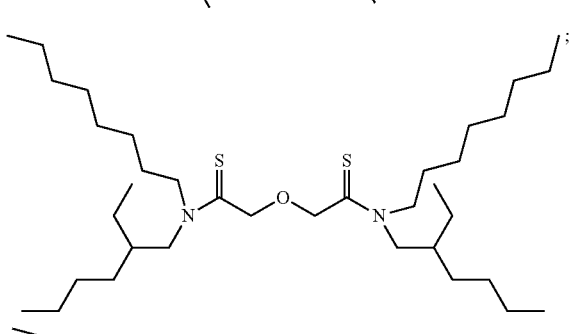

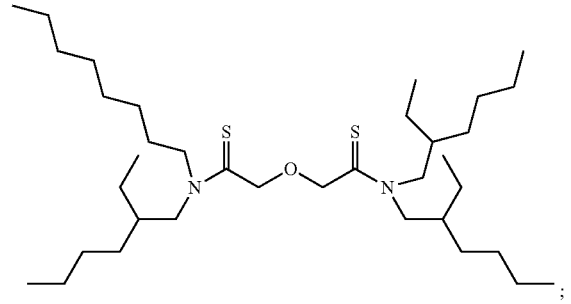

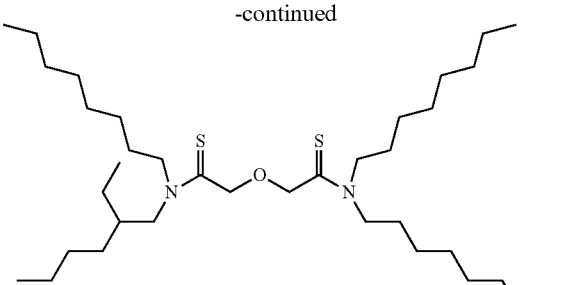

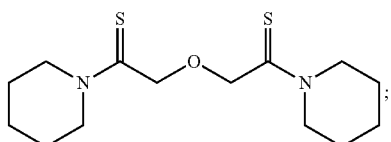

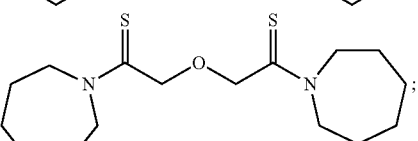

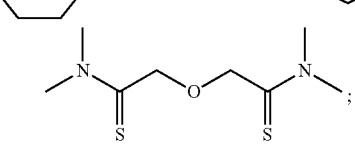

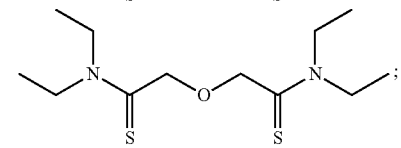

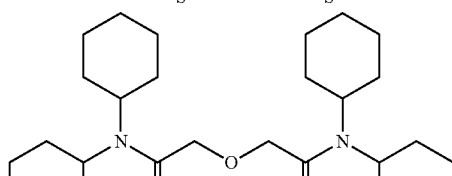

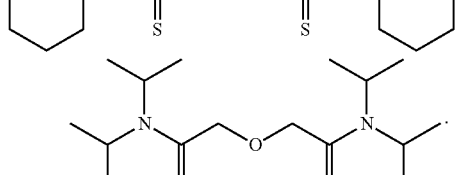

; or

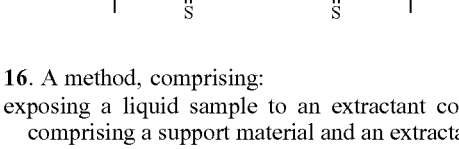

16. A method, comprising:
exposing a liquid sample to an extractant composition comprising a support material and an extractant having a structure satisfying Formula I

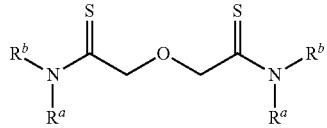

Formula I wherein each $R^a$ independently is hydrogen, aliphatic, heteroaliphatic, aromatic, aliphatic-aromatic, or heteroaliphatic-aromatic; and each $R^b$ independently is hydrogen, aliphatic, heteroaliphatic, aromatic, aliphatic-aromatic, or heteroaliphatic-aromatic, provided that at least one $R^a$ or one R$^b$ is aliphatic, heteroaliphatic, aromatic, aliphatic-aromatic, or heteroaliphatic-aromatic; and wherein the liquid sample is exposed to the composition for a time sufficient to promote formation of a complex between the extractant composition and a radioisotope, a metal, and/or any ion thereof present in the liquid sample;

separating the complex from the liquid sample;

exposing the complex to a solution having a pH sufficient to promote dissociation of the radioisotope, the metal, or any ion thereof from the extractant composition; and isolating the radioisotope, the metal, or any ion thereof.

17. The method of claim 16, wherein the radioisotope is protactinium, niobium, a protactinium ion, a niobium ion, or any combination thereof; and wherein the sample comprises thorium, iron, zinc, any ion thereof, or any combination thereof.

18. The method of claim 16, wherein the metal is gold, platinum, silver, palladium, any ion thereof, or any combination thereof; and wherein the sample comprises thorium, iron, zinc, any ion thereof, or any combination thereof.

19. A compound having a structure satisfying Formula I

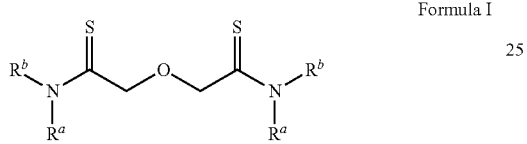

Formula I wherein each R$^a$ independently is hydrogen, aliphatic, heteroaliphatic, aromatic, aliphatic-aromatic, or heteroaliphatic-aromatic; and each R$^b$ independently is hydrogen, aliphatic, heteroaliphatic, aromatic, aliphatic-aromatic, or heteroaliphatic-aromatic, provided that at least one R$^a$ or one R$^b$ is aliphatic, heteroaliphatic, aromatic, aliphatic-aromatic, or heteroaliphatic-aromatic and further provided that the compound is not or is other than

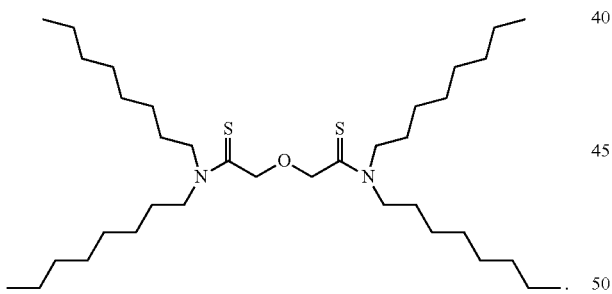

20. The compound of claim 19, wherein the compound is

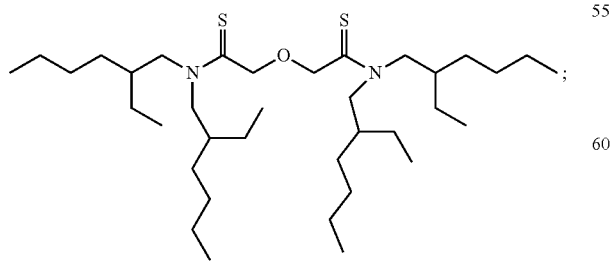

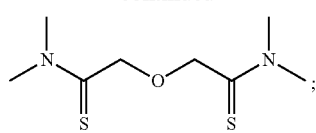

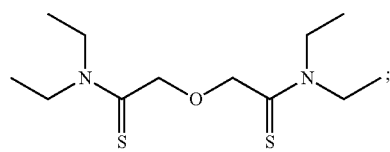

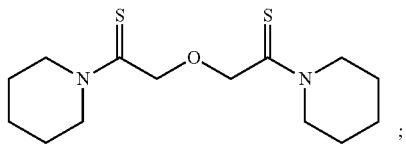

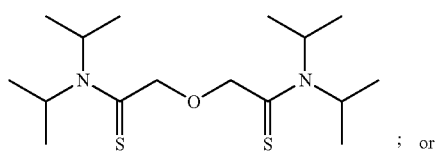

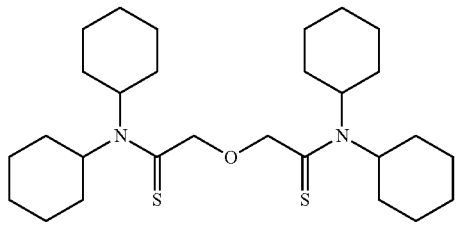

; or

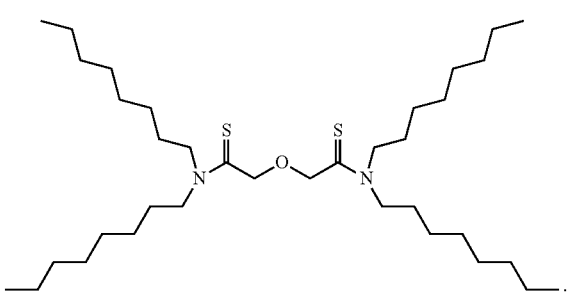 [SMILES: CCCCCCCCN(CCCCCCCC)C(=S)COCC(=S)N(CCCCCCCC)CCCCCCCC]

21. The composition of claim 1, wherein the extractant is not or is other than